(12) United States Patent
Malka et al.

(10) Patent No.: US 10,955,423 B2
(45) Date of Patent: Mar. 23, 2021

(54) METHODS OF ESTIMATING BLOOD GLUCOSE AND RELATED SYSTEMS

(71) Applicant: The General Hospital Corporation, Boston, MA (US)

(72) Inventors: Roy Malka, Newton, MA (US); John M. Higgins, Cambridge, MA (US); David M. Nathan, West Newton, MA (US)

(73) Assignee: The General Hospital Corporation, Boston, MA (US)

( * ) Notice: Subject to any disclaimer, the term of this patent is extended or adjusted under 35 U.S.C. 154(b) by 301 days.

(21) Appl. No.: 16/061,951

(22) PCT Filed: Dec. 15, 2016

(86) PCT No.: PCT/US2016/066860
§ 371 (c)(1),
(2) Date: Jun. 13, 2018

(87) PCT Pub. No.: WO2017/106461
PCT Pub. Date: Jun. 22, 2017

(65) Prior Publication Data
US 2018/0364262 A1 Dec. 20, 2018

Related U.S. Application Data

(60) Provisional application No. 62/379,942, filed on Aug. 26, 2016, provisional application No. 62/267,588, filed on Dec. 15, 2015.

(51) Int. Cl.
*G01N 33/72* (2006.01)
*G01N 33/555* (2006.01)
*A61B 5/145* (2006.01)

(52) U.S. Cl.
CPC ......... *G01N 33/723* (2013.01); *G01N 33/555* (2013.01); *G01N 33/726* (2013.01); *A61B 5/14532* (2013.01); *G01N 2800/042* (2013.01)

(58) Field of Classification Search
CPC .. G01N 33/723; G01N 33/555; G01N 33/726; G01N 2800/042; A61B 5/14532
See application file for complete search history.

(56) References Cited

U.S. PATENT DOCUMENTS

| | | | |
|---|---|---|---|
| 5,017,497 A | 5/1991 | Gerard de Grooth et al. |
| 5,266,269 A | 11/1993 | Niiyama et al. |
| 5,369,014 A | 11/1994 | Brugnara et al. |
| 5,378,633 A | 1/1995 | von Behrens et al. |
| 5,631,165 A | 5/1997 | Chupp et al. |
| 5,812,419 A | 9/1998 | Chupp et al. |
| 5,822,715 A | 10/1998 | Worthington et al. |
| 6,030,838 A | 2/2000 | Telmissani |
| 6,228,652 B1 | 5/2001 | Rodriguez et al. |
| 6,320,656 B1 | 11/2001 | Ferrante et al. |
| 6,524,858 B1 | 2/2003 | Zelmanovic et al. |
| 7,324,194 B2 | 1/2008 | Roche et al. |
| 7,981,681 B2 | 7/2011 | Champseix et al. |
| 8,481,323 B2 | 7/2013 | Tyvoll et al. |
| 2004/0152199 A1 | 8/2004 | Kendall et al. |
| 2006/0203226 A1 | 9/2006 | Roche et al. |
| 2007/0099301 A1 | 5/2007 | Tyvoll et al. |
| 2007/0172956 A1 | 7/2007 | Magari et al. |
| 2008/0153170 A1 | 6/2008 | Garrett et al. |
| 2008/0158561 A1 | 7/2008 | Vacca et al. |
| 2008/0268494 A1 | 10/2008 | Linssen |
| 2011/0070210 A1 | 3/2011 | Andrijauskas |
| 2011/0070606 A1 | 3/2011 | Winkelman et al. |
| 2011/0077871 A1 | 3/2011 | Fukuma et al. |
| 2011/0149061 A1 | 6/2011 | Wardlaw et al. |
| 2011/0164803 A1 | 7/2011 | Wang et al. |
| 2011/0178716 A1 | 7/2011 | Krockenberger et al. |
| 2011/0190143 A1 | 8/2011 | Payen de la Garanderie et al. |
| 2012/0263369 A1 | 10/2012 | Xie et al. |
| 2013/0236566 A1 | 9/2013 | Higgins |
| 2014/0187887 A1* | 7/2014 | Dunn ................ G16H 40/67 600/365 |
| 2015/0160188 A1 | 6/2015 | Krockenberger et al. |
| 2015/0330963 A1 | 11/2015 | Vidal et al. |
| 2017/0108487 A1 | 4/2017 | Higgins |
| 2018/0187235 A1 | 7/2018 | Higgins |

FOREIGN PATENT DOCUMENTS

| | | |
|---|---|---|
| JP | 1995-105166 | 4/1995 |
| JP | 1999-326315 | 11/1999 |
| JP | A-2005-503559 | 2/2005 |
| JP | 2006-516735 | 7/2006 |
| JP | 2006-527199 | 11/2006 |
| JP | 2009-36587 | 2/2009 |
| JP | 2009-510402 | 3/2009 |
| JP | 2009-524068 | 6/2009 |
| JP | 2009-524069 | 6/2009 |
| JP | 2010-526873 | 8/2010 |
| WO | 2001/77140 | 10/2001 |
| WO | WO 03/025583 | 3/2003 |
| WO | WO 2007/0084977 | 7/2007 |
| WO | WO 2011/057744 | 5/2011 |
| WO | WO 2012/037524 | 3/2012 |
| WO | WO 2014/074889 | 5/2014 |

OTHER PUBLICATIONS

International Search Report and Written Opinion dated Mar. 2, 2017 in international application No. PCT/US2016/066860, 12 pgs.
"How to read complete blood count," JIM, 2006, 16: 792-795 (with English abstract).
Adams et al., "Cardiac troponin I. A marker with high specificity for cardiac injury," Circulation, 1993, 88: 101-106.

(Continued)

*Primary Examiner* — Christopher Adam Hixson
(74) *Attorney, Agent, or Firm* — Fish & Richardson P.C.

(57) ABSTRACT

A method includes estimating a value of a parameter indicative of an age or lifespan of a population of red blood cells of a subject, estimating a value of average glucose (AG) of the subject based on (i) the value of the parameter and (ii) a value indicative of an amount of glycated hemoglobin (HbA1c) of the subject, and providing information for treatment or diagnosis of a hyperglycemia condition of the subject based on the estimated value of AG.

17 Claims, 11 Drawing Sheets

(56) References Cited

OTHER PUBLICATIONS

Ali et al., "H2RM: A Hybrid Rough Set Reasoning Model for Prediction and Management of Diabetes Mellitus," Sensors, Jul. 2015, 15: 15921.

Allen et al., "Validation and Potential 10 Mechanisms of Red Cell Distribution Width as a Prognostic Marker in Heart Failure," J Card Fail, Mar. 2010, 16:230-238.

Altenbaugh, "Suitability and Utility of Computational Analysis Tools: characterization of Erythrocyte Parameter Variation," Pacific Symposium on Biocomputing, 2003, 8: 104-115.

American Diabetes Association, "Standards of medical care in diabetes—2010," Diabetes Care, 2010, 33: S11-S61.

Anderson et al, "Usefulness of a complete blood count-derived risk score to predict incident mortality in patients with suspected cardiovascular disease," Am J Cardiol, 2007, 99: 169-174.

Apple et al., "Analytical Characteristics of High-Sensitivity Cardiac Troponin Assays," Clin. Chem, 2011, 58: 54-61.

Athens et al., "Leukokinetic Studies. IV. The Total Blood, Circulating and Marginal Granulocyte Pools and the Granulocyte Turnover Rate in Normal Subjects," J. Clin. Invest, 1961, 40: 989-995.

Bainton et al., "Developmental Biology of Neutrophils and Eosinophils," Inflammation. Basic Principles and Clinical Correlates, Chapter 2, 1999, 13-34.

Barua et al,, "The relationship between fasting plasma glucose and HbA(1c) during intensive periods of glucose control in antidiabetic therapy," J. Theor. Biol, Dec. 2014, 363: 158.

Beach, "A theoretical model to predict the behavior of glycosylated hemoglobin levels," Journal of Theoretical Biology, 1979, 81: 547-561.

Bergman, "Toward Physiological Understanding of Glucose-Tolerance—Minimal-Model Approach," Diabetes, 1989, 38: 1512-1527.

Bergman, et al., "Physiologic Evaluation of Factors Controlling Glucose-Tolerance in Man—Measurement of Insulin Sensitivity and Beta-Cell Glucose Sensitivity from the Response to Intravenous Glucose," Journal of Clinical Investigation, 1981, 68: 1456-1467.

Beutler and Waalen, "The definition of anemia: what is the lower limit of normal of the blood hemoglobin concentration?," Blood, 2006, 107: 1747-1750.

Bunn et al., "The biosynthesis of human hemoglobin A1c. Slow glycosylation of hemoglobin in vivo," Journal of Clinical Investigation, 1976, 57: 1652-1659.

Bunn et al., "The glycosylation of hemoglobin: relevance to diabetes mellitus," Science, Apr. 1978, 200:21-27.

Carstairs, "The Human Small Lymphocyte: Its Possible Pluripoilntial Quality," Lancet, 1962, 279: 829-832.

Casanova-Acebes et al., "Rhythmic Modulation of the Hematopoietic Niche through Neutrophil Clearance," Cell, 2017, 153: 1025-1035.

Cohen et al, "Red cell life span heterogeneity in hematologically normal people is sufficient to alter HbA1 c," Blood, Nov. 2008, 112:4284-4291.

Cohen et al., "Discordance between HbA(1c) and fructosamine—Evidence for a glycosylation gap and its relation to diabetic nephropathy," Diabetes Care, Jan. 2003, 26: 163-167.

Cohen et al., "Is poor glycemic control associated with reduced red blood cell lifespan?," Diabetes Care, 2004, 27: 1013-1014.

Cook, "Diagnosis and management of iron-deficiency anaemia," Best Practice & Research Clinical Haematology, vol. 18, p. 319-332, 2005.

International Search Report and Written Opinion dated Jun. 27, 2017 in International Application No. PCT/US2017/026695, 18 pgs.

Cornbleet, "Clinical utility of the band count," Clin. Lab. Med, 2002, 22: 101-136.

Crane et al., "Glucose levels and risk of dementia," New England Journal of Medicine, 2013, 369: 540-548.

Cronkite and Vincent, "Granulocytopoiesis," Series Haematologica, 1969, II: 3-43.

D'Onofrio et al., "Simultaneous Measurement of Reticulocyte and Red-Blood-Cell Indexes in Healthy-Subjects and Patients with Microcytic Anemia," Blood, 1995, 85(3):818-823.

Damiano et al., "A comparative effectiveness analysis of three continuous glucose monitors: the Navigator, G4 Platinum, and Enlite," Journal of Diabetes Science and Technology, July 2014, 8: 699-708

Daubert and Jeremias, The utility of troponin measurement to detect myocardial infarction: review of the current findings, Vasc. Health Risk Manag, 2010, 6: 691-699.

DCCT Research Group, "The effect of intensive treatment of diabetes on the development and progression of long-term complications in insulin-dependent diabetes mellitus," N Engl J Med, 1993, 329: 977-986.

De Smet et al., "Use of the Cell-Dyn Sapphire Hematology Analyzer for Automated Counting of Blood Cells in Body Fluids," Am. J. Clin. Pathol, 2010, 133: 291-299.

Eliaz et al., "Modeling failure of metallic glasses due to hydrogen embrittlement in the absence of external loads," Acta Materialia, Jan. 2004, 52: 93-105.

El-Khatib et al., "A Bihormonal Closed-Loop Artificial Pancreas for Type 1 Diabetes," Science Translational Medicine, Apr. 2010, 2: 27ra27.

Engstrom et al, "Red cell distribution width, haemoglobin Ale and incidence of diabetes mellitus," Journal of Internal Medicine, Aug. 2014, 276: 174-183.

European Office Action in European Application No. 11826059, dated Jan. 29, 2016, 8 pages.

European Search Report in Application No. 15803598.0, dated Nov. 27, 2017, 10 pages.

European Search Report in Application No. 17160801.1, dated Jan. 16, 2018, 14 pages.

European Search Report in Application No. 1716081.1, dated Sep. 25, 2017.

Felker et al, "Red cell distribution width as a novel prognostic marker in heart failure—Data from the CHARM program and the Duke Databank," J Am Coll Cardiol, 2007, 50:40-47.

Franco et al., "Changes in the properties of normal human red blood cells during in vivo aging," Am J Hematol, Jan. 2013, 88:44-51.

Franco, "The measurement and importance of red cell survival," Am J Hematol, Feb. 2009, 84:109-114.

Gardner and Benz Jr., "Anemia of chronic diseases." In: Hoffman et al., eds. Hematology: Basic Principles and Practice. 5th ed. Philadelphia, Pa: Elsevier Churchill Livingstone; 2008:chap 37, 8 pages.

Garner et al., "Genetic influences on F cells and other hematologic variables: a twin heritability study," Blood, 2000, 95(1):342-346.

Georga et al., "Evaluation of short-term predictors of glucose concentration in type 1 diabetes combining feature ranking with regression models," Medical & Biological Engineering & Computing, Dec. 2015, 53: 1305.

George, "Malignant or Benign Leukocytosis," American Society of Hematology, 2012, 475-484.

Gifford et al., "A detailed study of time-dependent changes in human red blood cells: from reticulocyte maturation to erythrocyte senescence," Br J Haematol., 2006, 135(3):395-404.

Gijsberts et al., "Hematological Parameters Improve Prediction of Mortality and Secondary Adverse Events in Coronary Angiography Patients: A Longitudinal Cohort Study," Medicine (Baltimore), Nov. 2015, 94: e1992.

Given et al., "Measurement error in estimated average glucose: a novel approach," Clinical Chemistry and Laboratory Medicine, Jul. 2014, 52: E147-E150.

Golub et al., "Developmental plasticity of red blood cell homeostasis," Am. J. Hematol, May 2014, 89: 459.

Gould et al., "Investigation of the mechanism underlying the variability of glycated haemoglobin in non-diabetic subjects not related to glycaemia," Clin. Chim. Acta, Apr. 1997, 260: 49-64.

Gram-Hansen et al, "Glycosylated Hemoglobin (HbA1c) as an Index of the Age of the Erythrocyte Population in NonDiabetic Patients," Eur J Haematol, 1990, 44:201-203.

(56) References Cited

OTHER PUBLICATIONS

Harrington et al., "Iron Deficiency Anemia, β-Thalassemia Minor, and Anemia of Chronic Disease: A Morphologic Reappraisal," Am J Clin Pathol., Dec. 2008, 129:466-471.

Hempe et al., "High and low hemoglobin glycation phenotypes in type 1 diabetes: a challenge for interpretation of glycemic control," Journal of Diabetes and Its Complications, 2002, 16: 313-320.

Higgins and Bunn, "Kinetic analysis of the nonenzymatic glycosylation of hemoglobin," Journal of Biological Chemistry, 1981, 256: 5204-5208.

Higgins and Mahadevan, "Physiological and Pathological Population Dynamics of Circulating Human Red Blood Cells," PNAS, Nov. 2010, 107(47):20587-20595.

Hoelzel et al., "IFCC reference system for measurement of hemoglobin A1c in human blood and the national standardization schemes in the United States, Japan, and Sweden: a method-comparison study," Clinical Chemistry, 2004, 50: 166-174.

Hoffstein et al., "Degranulation, membrane addition, and shape change during chemotactic factor-induced aggregation of human neutrophils," J. Cell Biol, 1982, 95: 234-241.

Horne et al., "Which White Blood Cell Subtypes Predict Increased Cardiovascular Risk?," J. Am. Coll. Cardiol, 2005, 45: 1638-1643.

Horne, "A Changing Focus on the Red Cell Distribution Width: Why Does It Predict Mortality and Other Adverse Medical Outcomes? ," Cardiology, 2012, 122:213-215.

Horne, "The Red Cell Distribution Width: What Is Its Value for Risk Prognostication and for Understanding Disease Pathophysiology?," Cardiology, 2011, 119:140-141.

Huang et al., "Using Hemoglobin A1C as a Predicting Model for Time Interval from Pre-Diabetes Progressing to Diabetes," Plos One, Aug. 2014, 9.

IDF Diabetes Altas, Seventh Edition, International Diabetes Federation, 2015, 140 pages.

International Preliminary Report on Patentability in International Application No. PCT/US2011/052038, dated Mar. 19, 2013, 7 pages.

International Preliminary Report on Patentability in International Application No. PCT/US2015/034508, dated Dec. 6, 2016, 9 pages.

International Preliminary Report on Patentability in International Application No. PCT/US2016/066860, dated Jun. 19, 2018, 8 pages.

International Preliminary Report on Patentability in International Application No. PCT/US2017/026695, dated Oct. 18, 2018, 10 pages.

International Search Report and Written Opinion in International Application No. PCT/US2016/066860, dated Mar. 2, 2017, 12 pages.

International Search Report and Written Opinion issued in PCT/US2011/052038 dated May 2, 2012, 11 pages.

International Search Report and Written Opinion dated Aug. 27, 2015 in International application No. PCT/US2015/034508, 13 pages.

Israeli Office Action in Israel Application No. 225275, dated Dec. 13, 2015, 7 pages (with English translation).

Jansen et al, "Determinants of HbA1c in nondiabetic Dutch adults: genetic loci and clinical and lifestyle parameters, and their interactions in the lifelines cohort study," Journal of Internal Medicine, 2013, 273:283-293.

Jansen et al., "Determinants of HbA1c in nondiabetic Dutch adults: genetic loci and clinical and lifestyle parameters, and their interactions in the lifelines cohort study," Journal of Internal Medicine, 2013, 273: 283.

Japanese Office Action in Application No. 2017-144114, dated May 15, 2018, 9 pages (with English translation).

Japanese Office Action in Japanese Application No. 2015-189343, dated Sep. 6, 2016, 11 pages (with English translation).

Jelkmann and Lundby, "Blood doping and its detection," Blood, Sep. 2011, 118(9):2395-2404.

Jopang et al., "False Positive Rates of Thalassemia Screening in Rural Clinical Setting: 10-Year Experience in Thailand," Southeast Asian J Trop. Med. Public Health, 2009, 40(3):576-580.

Kakkar and Makkar, "Red Cell Cytograms Generated by an AD VIA 120 Automated Hematology Analyzer: Characteristic Patterns in Common Hematological Conditions," Labmedicine, 2009, 40: 549-555.

Kawaguchi et al., "Band neutrophil count and the presence and severity of coronary atherosclerosis," Am. Heart J, 1996, 132: 9-12.

Khera et al., "Use of an oral stable isotope label to confirm variation in red blood cell mean age that influences HbA1c interpretation," Am. J. Hematol, 2015, 90: 50-55.

Kim et al., "Association Between Iron Deficiency and A1C Levels Among Adults Without Diabetes in the National Health and Nutrition Examination Survey, 1999-2006," Diabetes Care, Jan. 2010, 33: 780-785.

Kitcharoen et al., "A New Screening Program for Thalassemias in Thailand Based on the Complete Blood Count," Medical Online, 1994, 17: 178-183.

Kleophas, "Dose tailoring strategies in haemodialysis patients: a discussion of case histories," Nephrol Dial Transplant, vol. 20 [Suppl 6], p. vi31-vi36, 2005.

Kochanek et al., "Mortality in the United States, 2013," NCHS Data Brief, No. 178. Hyattsville, MD: National Center for Health Statistics, 2014, 8 pages.

Koren-Morag et al., "White blood cell count and the incidence of ischemic stroke in coronary heart disease patients," Am. J. Med, 2005, 118: 1004-1009.

Kovatchev et al., "Accuracy and Robustness of Dynamical Tracking of Average Glycemia (A1c) to Provide Real-Time Estimation of Hemoglobin A1c Using Routine Self-Monitored Blood Glucose Data," Diabetes Technol. Ther, May 2014, 16: 303-309.

Ladyzynski et al, "Hemoglobin Glycation Rate Constant in Non-diabetic Individuals," Ann Biomed Eng, 2011, 39:2721-2734.

Ladyzynski et al, "Validation of hemoglobin glycation models using glycemia monitoring in vivo and culturing of erythrocytes in vitro," Ann Biomed Eng, 2008, 36: 1188-1202.

Ladyzynski et al., "Hemoglobin glycation rate constant in non-diabetic individuals," Annals of Biomedical Engineering, 2011, 39: 2721.

Lang et al., "Mechanisms of suicidal erythrocyte death," Cell Physiol Biochem., 2005, 15(5):195-202.

Lenters-Westra and Slingerland, "Six of Eight Hemoglobin A(1c) Point-of-Care Instruments Do Not Meet the General Accepted Analytical Performance Criteria," Clinical Chemistry, Jan. 2010, 56: 44-52.

Leslie and Cohen, "Biologic variability in plasma glucose, hemoglobin A1e, and advanced glycation end products associated with diabetes complications," Journal of Diabetes Science and Technology, Jul. 2009, 3:635-643.

Lew et al., "Generation of Normal Human Red-Cell Volume, Hemoglobin Content, and Membrane Area Distributions by "Birth" or Regulation," Blood, 1995, 86(1):334-341.

Lippi et al., "Stability of blood cell counts, hematologic parameters and reticulocytes indexes on the Advia A120 hematologic analyzer," J Lab. Clin. Med., 2005, 146(6):333-340.

Lledó-Garcia et al., "A semi-mechanistic model of the relationship between average glucose and HbA1c in healthy and diabetic subjects." Journal of Pharmacokinetics and Pharmacodynamics, 2013,14 pages.

Lozoff et al., "Long-Term Developmental Outcome of Infants with Iron-Deficiency," N Engl J Med, Sep. 1991, 325:687-694.

Lundby, "Erythropoietin treatment elevates haemoglobin concentration by increasing red cell volume and depressing plasma volume," J Physiol, 578, Jan. 2007, 309-314.

Mackay, "Homing of naive, memory and effector lymphocytes," Curr. Opin. Immunol, 1993, 5: 423-427.

Madjid et al., "Leukocyte count and coronary heart disease," J. Am. Coll. Cardiol, 2004, 44: 1945-1956.

Malka et al., "In vivo volume and hemoglobin dynamics of human red blood cells," PLoS Comput. Biol, 2014, 10: e1003839.

(56) References Cited

OTHER PUBLICATIONS

Matthews et al., "Homeostasis model assessment: insulin resistance and beta-cell function from fasting plasma glucose and insulin concentrations in man," Diabetologia, Jul. 1985, 28: 412-419.
Menezes et al., "Targeted clinical control of trauma patient coagulation through a thrombin dynamics model," Sci. Transl. Med, 2017, 9: eaaf5045.
Menon et al., "Leukocytosis and adverse hospital outcomes after acute myocardial infarction," Am. J. Cardiol, 2003, 92: 368-372.
Milbrandt et al., "Predicting late anemia in critical illness," Crit. Care, 2006, 10(1), 8 pages.
Mock et al., "Measurement of Posttransfusion Red Cell Survival With the Biotin Label," Transf Med Rev, Jul. 2014, 28: 114-125.
Mortensen et al., "Glucosylation of human haemoglobin a. dynamic variation in HbA 1c described by a biokinetic model," Clinica Chimica Acta, 1984, 136: 75.
Mosior et al., "Critical cell volume and shape of bovine erythrocytes," General Physiology and Biophysics, Oct. 1992, 499-506.
Nathan et al., "Translating the A1C assay into estimated average glucose values," Diabetes Care, 2008, 31: 1-6.
Neumann and Nurse, "Nuclear size control in fission yeast," J. Cell Biol, 2007, 179: 593-600.
Ntaios et al., "Discrimination indices as screening tests for beta-thalassemic Trait," Ann. Hematol., 2007, 86(7):487-491.
Office Action in European Application No. 15803598.0, dated Oct. 16, 2018, 7 pages.
Office Action in Israeli Application No. 225275, dated Jan. 8, 2017, 4 pages, with English translation.
Office Action in U.S. Appl. No. 13/823,338, dated Apr. 7, 2017, 17 pages.
Office Action issued in JP2013-529382 dated May 26, 2015, 9 pages (with English translation).
Osterman-Golkar and Vesper, "Assessment of the relationship between glucose and A1c using kinetic modeling," Journal of Diabetes and its Complications, 2006, 20: 285-294.
Pande et al., "The sweep constant concept in phase coarsening," Metallurgical and Materials Transactions, Sep. 1998, 29: 2395-2398.
Pascual-Figal et al., "Red blood cell distribution width predicts new-onset anemia in heart failure patients," Int J Cardiol, 2012, 160: 196-200.
Patel et al., "Modulation of red blood cell population dynamics is a fundamental homeostatic response to disease : Modulation of red blood cell population dynamics," American Journal of Hematology, May 2015, 90: 422-428.
Patel et al., "Red Blood Cell Distribution Width and the Risk of Death in Middle-aged and Older Adults," Arch Intern Med, Mar. 2009, 169:515-523.
Perlstein et al., "Red Blood Cell Distribution 30 Width and Mortality Risk in a Community-Based Prospective Cohort," Arch Intern Med, Mar. 2009, 169:588-594.
Piva et al., "Automated reticulocyte counting: state of the art and clinical applications in the evaluation of erythropoiesis," Clinical Chemistry and Laboratory Medicine, Oct. 2010, 48:1369-1380.
Prommer, "Total Hemoglobin Mass—A New Parameter to Detect Blood Doping," Medicine & Science in Sports & Exercise, vol. 40, p. 2112-2118, 2008.
Rockey and Cello, "Evaluation of the Gastrointestinal Tract in Patients With Iron-Deficiency Anemia," New Engl J Med., Dec. 1992, 329(23):1691-1695.
Rohlfing et al., "Biological variation of glycohemoglobin," Clinical Chemistry, Jul. 2002, 48: 1116-1118.
Sacks, "Hemoglobin A1c in diabetes: panacea or pointless?," Diabetes, 2013, 62: 41-43.
Segura et al., "Current strategic approaches for the detection of blood doping practices," Forensic Sci Int., 2011, 42-48.
Sens and Gov, "Force balance and membrane shedding at the red blood-cell surface," Phys Rev Lett., 2007, 98(018102):1-4.
Shiga et al., "Laboratory Diagnosis of Anemia and Related Diseases Using Multivariate Analysis," American Journal of Hematology, 1997, 54: 108-117.
Spell et al., "The value of a complete blood 5 count in predicting cancer of the colon," Cancer Detect Prev, 2004, 28:37-42.
Statland et al., "Evaluation of Biologic Sources of Variation of Leukocyte Counts and Other Hematologic Quantities Using Very Precise Automated Analyzers," Am. J. Clin. Pathol, 1978, 69: 48-54.
Supplementary European Search Report issued in EP 11826059 dated Feb. 21, 2014, 18 pages.
Tahara and Shima, "Kinetics of HbA(1c), glycated albumin, and fructosamine and analysis of their weight-functions against preceding plasma-glucose level," Diabetes Care, Apr. 1995, 18: 440-447.
Tamhane et al., "Association Between Admission Neutrophil to Lymphocyte Ratio and Outcomes in Patients With Acute Coronary Syndrome," Am. J. Cardiol, 2008, 102: 653-657.
Thompson et al., "Size-dependent B lymphocyte subpopulations: relationship of cell volume to surface phenotype, cell cycle, proliferative response, and requirements for antibody production to TNP-Ficoll and TNP-BA," J. Immunol, 1984, 133: 2333-2342.
Tzur et al., "Cell Growth and Size Homeostasis in Proliferating Animal Cells," Science, 2009, 325: 167-171.
UK Prospective Diabetes Study (UKPDS) Group, "Intensive blood-glucose control with sulphonylureas or insulin compared with conventional treatment and risk of complications in patients with type 2 diabetes (UKPDS 33)," The Lancet, 1998, 352: 837-853.
Veeranna et al., "The Association of Red Cell Distribution Width with Glycated Hemoglobin among Healthy Adults without Diabetes Mellitus," Cardiology, 2012, 122:129-132.
Wang et al., "Closed-Loop Control of Artificial Pancreatic beta-Cell in Type 1 Diabetes Mellitus Using Model Predictive Iterative Learning Control," IEEE Trans. Biomed. Eng, Feb. 2010, 57: 211-219.
Wang et al., "Heterogeneity of human blood monocyte: two subpopulations with different sizes, phenotypes and functions," Immunology, 1992, 77: 298-303.
Waugh et al., "Rheologic properties of senescent erythrocytes: loss of surface area and volume with red blood cell age," Blood, 1992, 79(5):1351-1358.
Webster et al., "Sizing up the nucleus: nuclear shape, size and nuclear-envelope assembly," J. Cell Sci, 2009, 122: 1477-1486.
Wilkinson and Grand, "Comparison of amino acid sequence of troponin I from different striated muscles," Nature, 1978, 271: 31-35.
Willekens et al., "Erythrocyte vesiculation: a self-protective mechanism? ," Br J Haematol, Apr. 2008, 141:549-556.
Willekens et al., "Hemoglobin loss from erythrocytes in vivo results from spleen-facilitated vesiculation," Blood, 2003, 101(2):747-751.
Willekens et al., "Liver Kupffer cells rapidly remove red blood cell-derived vesicles from the circulation by scavenger receptors," Blood, 2005, 105(5):2141-2145.
Yudkin et al., "Unexplained Variability of Glycated Hemoglobin in Nondiabetic Subjects Not Related to Glycemia," Diabetologia, Apr. 1990, 33: 208-215.
Yunoki et al., "MCH is useful for early diagnosis of thalassemia," 2003, 44: 771 PS-1-169 (with English Abstract).
Zecchin et al., "Jump Neural Network for Real-Time Prediction of Glucose Concentrationin," in Artificial Neural Networks, 2nd Edition, 2015, 1260: 245-259.
Zenker et al., "From inverse problems in mathematical physiology to quantitative differential diagnoses," PLoS Comput. Biol., 2007, 3(11):2072-2086.
EP Office Action in European Appln. No. 17160801, dated Apr. 2, 2020, 5 pages.

\* cited by examiner

METHODS OF ESTIMATING BLOOD GLUCOSE AND RELATED SYSTEMS

CLAIM OF PRIORITY

This application is a § 371 National Stage Application of PCT/US2016/066860, filed Dec. 15, 2016, which claims the benefit of U.S. Provisional Patent Application Ser. Nos. 62/267,588, filed on Dec. 15, 2015, and 62/379,942, filed Aug. 26, 2016. The entire contents of the foregoing are hereby incorporated by reference in their entireties.

STATEMENT OF GOVERNMENT RIGHTS

This work was supported in part by NIH grant DP2DK098087. The United States government may have certain rights in the invention

TECHNICAL FIELD

This specification relates to methods of estimating blood glucose and related systems for the same.

BACKGROUND

Diabetes mellitus is a growing global health burden affecting about 400 million people worldwide (5). A person's glycated hemoglobin fraction can reflect the average concentration of glucose in the blood over the past 2-3 months and can be used to determine the risk for diabetes-related complications in patients with type 1 or type 2 diabetes (6-8). An HbA1c greater than or equal to 6.5% is diagnostic for diabetes, and the treatment goal for most people with diabetes is an HbA1c less than 7% (9). HbA1c can be used to set specific therapeutic targets for all patients with diabetes with the goal of reducing complications. Specific HbA1c targets for women who develop diabetes during pregnancy, e.g., gestational diabetes, and for women with diabetes who become pregnant are established to reduce perinatal complications for the mother and congenital malformations in the infant. HbA1c is used to infer average glucose levels (AG) because continuous glucose measurements (CGM) are not routinely available and episodic measures of blood glucose do not accurately capture AG (10).

SUMMARY

In one aspect, a method includes estimating a value of a parameter indicative of an age or lifespan of a population of red blood cells of a subject, estimating a value of average glucose (AG) of the subject based on (i) the value of the parameter and (ii) a value indicative of an amount of glycated hemoglobin (HbA1c) of the subject, and providing information for treatment or diagnosis of a hyperglycemia condition of the subject based on the estimated value of AG.

In another aspect, a method includes estimating a value of a parameter indicative of an age or lifespan of a population of red blood cells of a subject, estimating a value of an amount of HbA1c of the subject based on (i) the value of the parameter and (ii) a value indicative of blood glucose concentration of the subject, and providing information for treatment or diagnosis of a hyperglycemia condition of the subject based on the estimated value of the amount of HbA1c.

In yet another aspect, a method includes estimating a value of a parameter indicative of an age or lifespan of a population of red blood cells of a subject based on a value indicative of an amount of HbA1c and a value indicative of a blood glucose concentration of the subject, and providing information for treatment or diagnosis of a blood disorder of the subject based on the estimated value of the parameter.

Implementations can include one or more of the features described below and herein elsewhere.

In some implementations, the value of the parameter is indicative of at least one of an average red blood cell age ($M_{RBC}$), a half-life of a red blood cell population, or an average red blood cell lifespan.

In some implementations, the value indicative of the amount of HbA1c is a second value indicative of the amount of HbA1c, and the value of the parameter is estimated based on a first value indicative of the amount of HbA1c and a value indicative of blood glucose concentration of the subject. In some cases, the first value indicative of the amount of HbA1c is measured at a first time after a time period in which the value indicative of blood glucose concentration of the subject is measured. In some cases, the first time is earlier than a second time at which the second value indicative of the amount of HbA1c is measured.

In some implementations, estimating the value of the parameter includes estimating the value of the parameter based on a plurality of measurements collected by a continuous glucose monitoring (CGM) device. In some cases, the measurements are collected over a period of time of at least 7 days.

In some implementations, the parameter is estimated based on a weighted average of multiple values indicative of blood glucose concentration of the subject. In some cases, the value indicative of the amount of HbA1c is a second value indicative of the amount of HbA1c, the value of the parameter is estimated based on a first value indicative of the amount of HbA1c, and the weighted average is determined based on times at which the values indicative of blood glucose concentration are measured relative to a time at which the first value indicative of the amount of HbA1c is measured.

In some implementations, the value indicative of the amount of HbA1c is measured from a blood sample of the subject including the population of red blood cells, the value indicative of the amount of HbA1c being indicative of an average the amount of HbA1c of the population of red blood cells.

In some implementations, the method further includes determining a subject-specific relationship between values indicative of blood glucose concentration and values indicative of the amount of HbA1c for the subject based on the parameter. The value of the AG is, for example, estimated based on the subject-specific relationship. In some cases, the subject-specific relationship is defined by at least one of a value of a glycation rate constant or a value of a reticulocyte HbA1c amount. In some cases, the subject-specific relationship is a linear relationship between the values indicative of AG and the values indicative of the amount of HbA1c. In some cases, the parameter defines a slope of the linear relationship between the values indicative of AG and the values indicative of the amount of HbA1c.

In some implementations, the information includes data representing an amount of insulin to administer to the subject.

In some implementations, the information includes data representing an amount of a medication to administer to the subject to treat the hyperglycemia condition.

In some implementations, the method further includes determining a diagnostic threshold for the hyperglycemia condition based on the parameter and the estimated value of AG. The information includes, for example, data representing a diagnosis of the hyperglycemia condition for the subject when the value indicative of the amount of HbA1c is above the diagnostic threshold. The parameter indicative of the age or lifespan of the population of red blood cells is, for example, indicative of at least one of an average red blood cell age ($M_{RBC}$), a half-life of a red blood cell population, or an average red blood cell lifespan. In some cases, the value indicative of blood glucose concentration is a second value indicative of blood glucose concentration, and the value of the amount of HbA1c is a second value of the amount of HbA1c. The value of the parameter is estimated, for example, based on a first value indicative of blood glucose concentration and a first value indicative of the amount of HbA1c. In some cases, the first value indicative of the amount of HbA1c is measured at a first time after a time period in which the first value indicative of blood glucose concentration of the subject is measured. In some cases, the first time is earlier than a second time at which the second value indicative of blood glucose concentration is measured.

In some implementations, the parameter is estimated based on a weighted average of multiple values indicative of blood glucose concentration of the subject, the estimated value indicative of the amount of HbA1c is a second value indicative of the amount of HbA1c, the value of the parameter is estimated based on a first value indicative of the amount of HbA1c, and the weighted average is determined based on times at which the values indicative of blood glucose concentration are measured relative to a time at which the first value indicative of the amount of HbA1c is measured.

In some implementations, the method further includes determining a subject-specific relationship between values indicative of blood glucose concentration and values indicative of the amount of HbA1c for the subject based on the parameter. The value of the amount of HbA1c is estimated, for example, based on the subject-specific relationship.

In some implementations, the subject-specific relationship is defined by at least one of a value of a glycation rate constant or a value of a reticulocyte HbA1c amount.

In some implementations, the method further includes determining a diagnostic threshold for the hyperglycemia condition based on the parameter and the value indicative of blood glucose concentration. The information includes, for example, data representing a diagnosis of the hyperglycemia condition for the subject when the estimated value of the amount of HbA1c is above the diagnostic threshold.

In some implementations, the value of the parameter is indicative of a subject-specific relationship between values indicative of blood glucose concentration and values indicative of the amount of HbA1c for the subject.

In some implementations, the information includes data representing an amount of erythropoiesis stimulating agents (ESA) or iron supplements to administer to the subject.

In some implementations, the information includes data representing an amount of a medication to administer to the subject to treat the blood disorder.

In some implementations, the blood disorder is anemia.

Advantages of the foregoing may include, but are not limited to, those described below and herein elsewhere. An average blood glucose concentration value can be more accurately estimated from the HbA1c value. In particular, the average blood glucose concentration value represented by any HbA1c value can be estimated in a manner that accounts for inter-individual variations that otherwise detract from the accuracy of the estimated AG level. As a result, treatment and diagnosis of pathological conditions that have a basis in these estimated values can be tailored for the subject. In particular, the estimated values can improve treatment and diagnosis of metabolic conditions, hyperglycemia conditions, hypoglycemia conditions, blood disorders, etc.

In some cases, the pathological conditions can be diagnosed earlier based on the estimated values even though the measurements may not indicate a diagnosis of the pathological condition. Treatment can be administered earlier, thereby improving health outcomes for the subject.

Furthermore, the accurate estimates of the values can enable measurements of the values to be avoided, thereby reducing the invasiveness that can be associated with some measurements. In one particular example, if the blood glucose concentration is measured using an implantable device, the blood glucose concentration can be measured for a short duration of time to provide baseline data for making future estimates of the blood glucose concentration. Because the future estimates can be made with measurement of the HbA1c amount, the future estimates can be made without measurements of blood glucose concentration, thereby avoiding the invasiveness of implanting the implantable device.

The management of diabetes is based on aiming for target HbA1c levels, usually measured every 3 months and more frequently during pregnancy. The HbA1c level represents the average glucose levels over the preceding 2-3 months. Translation of HbA1c into average glucose levels can be important because patients adjust their overall treatment and medications on a day-to-day basis based on self-monitored and laboratory tested glucose levels. Thus, understanding the average glucose level for an individual, calculated from the HbA1c level, is important to help guide treatment changes that will in turn be guided by glucose levels. Under-estimates of average glucose derived from the HbA1c level may mislead patients into being complacent with regard to their glucose control, subjecting them to the risk of long-term complications. Over-estimates of average glucose derived from the HbA1c assay may motivate patients to be overly aggressive in controlling their glucose levels, subjecting them to the risk of hypoglycemia. Therefore, improving the estimation of average glucose derived from HbA1c levels for individual patients is critical to improve management, long-term outcomes and safety for patients with diabetes.

Unless otherwise defined, all technical and scientific terms used herein have the same meaning as commonly understood by one of ordinary skill in the art. Methods and materials described herein are for illustration purposes; other suitable methods and materials known in the art can also be used. The materials, methods, and examples are not intended to be limiting. All publications, patent applications, patents, sequences, database entries, and other references mentioned herein are incorporated by reference in their entirety. References parenthetically cited throughout this disclosure are listed in the References section presented herein. In case of conflict, the present specification, including definitions, will control.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Diabetes mellitus is managed based on HbA1c levels, which in turn are used to estimate the levels of average glucose (AG) over the preceding 2-3 months. Diabetes can also be diagnosed based on the HbA1c level for a patient. The average glucose level can be estimated based on a regression equation derived from the measurement of HbA1c and glucose levels in many hundreds of patients with type 1 and type 2 diabetes. A substantial fraction of patients can have an actual average glucose that deviates from the value provided by the regression equation. Such inaccurate estimates can misinform patients and their providers such that some patients may undertreat their diabetes, while others may over-treat their diabetes, potentially with hypoglycemia as a result. As described herein, a subject-specific correction factor can be determined to improve the accuracy of AG estimates.

Glycation of hemoglobin occurs in a two-step process including the condensation of glucose with the N-terminal amino group of the hemoglobin beta chain to form a Schiff base and the rearrangement of the aldimine linkage to a stable ketoamine (11). The kinetics of this slow non-enzymatic post-translational modification can depend on the concentration of glucose. First-order kinetics (1, 11, 12) and irreversibility of HbA1c formation (2, 13) characterize this process. Hemoglobin in older RBCs has had more time to become glycated, and older RBCs therefore have higher glycated fractions. HbA1c is measured as an average over RBCs of all ages in the circulation and therefore depends on both AG and average red blood cell age. Other factors may also be involved, including glucose gradients across the RBC membrane, intracellular pH, and glycation rate constants.

As discussed herein, the glycation process of hemoglobin includes both glycemic and non-glycemic factors. A mechanistic mathematical model can quantify the dependence of HbA1c on the chemical kinetics of hemoglobin glycation in a population of RBCs in dynamic equilibrium. The model can form the basis of a subject-specific relationship for estimating HbA1c amount and blood glucose concentration. Using existing CGM data, model parameters for individual patients can be determined to develop the subject-specific relationship between HbA1c and blood glucose concentration. As described in the Examples section herein, the subject-specification relationship is validated for its use in estimating future AG accurately from future HbA1c for each individual subject. The accuracy of the subject-specific model estimates of AG are compared with those made using a standard regression method that does not account for glucose-independent variation.

Example System

Figure 9:
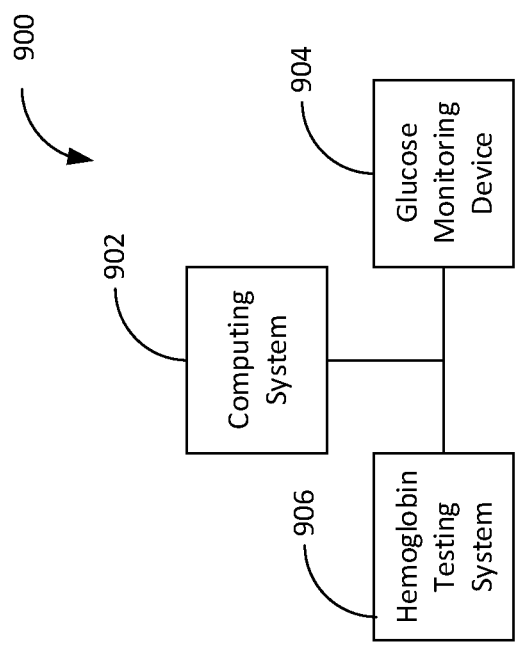
FIG. 9 is a block diagram of a diagnostic or treatment system.

FIG. 9 depicts a diagnostic or treatment system 900 operable to improve the accuracy of AG and HbA1c estimates in accordance to the technology described herein. The system 900 includes a computing system 902 that receives data from and transmits data to one or more other devices, including, for example, a glucose monitoring device 904 and a hemoglobin testing system 906.

The computing system 902 is capable of receiving and transmitting data from other devices in the system 900. The computing system 902 includes one or more servers that establish wired or wireless links with other devices of the system 900. The computing system 902 includes, for example, a portion of a network-accessible computing platform implemented as a computing infrastructure of processors, storage, software, data access, and so forth maintained and accessible through a communication network as described herein.

The computing system 902 includes, for example, a computing system associated with a medical facility, such as a hospital, a clinic, a medical laboratory, a testing or other medical facility where health care providers provide medical care to patients, e.g., including the subject. The computing system 902, for example, corresponds to a central computing system for the medical facility. The central computing system stores patient information including orders from the health care providers, information collected pertaining to the patients, diagnoses for the patients, test results for the patients, and other medical record information pertaining to the patients. In some cases, the computing system 902 serves as a central computing system that is connected to several different nodes across multiple different sites, e.g., associated with multiple medical facilities. Each medical facility includes a corresponding computing system connected to the computing system 902. The computing system 902 stores medical record information, the nodes receive the medical record information from the computing system 902 to provide the health care providers at the medical facilities with information to care for the patients.

In some examples, the computing system 902 includes a user terminal. The user terminal corresponds to, for example, a laptop, tablet computer, a desktop, or other appropriate workstation for a health care provider. The user terminal is operable by the health care provider to provide an input to the computing system 902 or to present information to the health care provider. The health care provider, for example, operates a keyboard, a mouse, or other user input device to provide data to the computing system 902. In some cases, the computing system 902 stores the data in a memory storage element for use at a later time. The computing system 902 provides information to the user terminal, which in turn presents the information to the health care provider through an appropriate user output device, e.g., in visual or audible format. The user output device corresponds to, for example, a computing display, a monitor, a speaker, or other appropriate user output device.

The glucose monitoring device 904 is capable of measuring a blood glucose concentration of the subject. The glucose monitoring device 904 is, for example, a portable continuous glucose monitoring device including a glucose sensor and a controller. In this regard, the subject using the glucose monitoring device 904 carries the glucose monitoring device 904 on a daily basis to monitor the subject's blood glucose concentration.

In some examples, the glucose monitoring device 904 is a continuous glucose monitoring (CGM) device worn on the subject. The glucose sensor is, for example, an implantable glucose sensor to be implanted under a skin of the subject. The controller of the glucose monitoring device 904 is worn externally on the subject while the implantable glucose sensor is worn by the patient such that a portion of the sensor is implanted under the skin of the subject. The sensor is worn for a period of time during which the glucose sensor generates measurements of blood glucose concentration of the subject. The glucose monitoring device 904 monitors the blood glucose concentration over a continuous period of time, for example, over 5 days to 2 months, e.g., 1 week to 2 weeks, 1 week to 1 month, 2 weeks to 6 weeks, etc. The controller of the glucose monitoring device 904 receives data representing the measurements from the glucose sensor. In some cases, the data are stored in a memory storage element associated with the glucose monitoring device 904.

In some cases, the glucose monitoring device 904 includes a user output device, such as a display, that provides visual indicators of values measured by the glucose monitoring device 904. The user output device, for example, presents an indicator of a level of the blood glucose concentration. The subject using the glucose monitoring device 904 is kept informed of his or her blood glucose concentrations through the user output device. Treatment for the hyperglycemia condition is administered or the subject is diagnosed with the hyperglycemia condition based on the blood glucose concentrations, e.g., to maintain blood glucose concentrations within a desired range. In some cases, the value of the HbA1c of the subject is estimated based on the blood glucose concentrations, and the treatment is administered or the patient is diagnosed based on the estimated value of the HbA1c.

In some examples, the subject is diagnosed with a hyperglycemia condition when the blood glucose concentration is greater than 200 mg/dL. In some examples, the user output device presents information indicative of the HbA1c value of the patient estimated from the blood glucose concentration. A treatment is performed based on the estimated HbA1c value. In some examples, the target value of the HbA1c to achieve using the treatment is 7%, e.g., between 6.75% and 7.25%. In particular, treatment is administered to the subject to decrease the estimated value of the HbA1c to below the target value of HbA1c. In some examples, the diagnostic threshold to diagnose the subject with a hyperglycemia condition is 7%, e.g., between 6.25% and 6.75%. In particular, an estimated value of the HbA1c above the diagnostic threshold is indicative of the subject having the hyperglycemia condition.

The glucose monitoring device 904 is configured to generate a measurement of a value of a blood glucose concentration from a subject. The glucose monitoring device 904, for example, receives a medical fluid sample from the subject and measures the value of the glucose concentration in the medical fluid sample. The medical fluid sample includes, for example, whole blood, plasma, serum, interstitial fluid, or other fluid that can be assayed to provide a measure indicative of a glucose concentration in blood of the subject.

In some examples, the controller of the glucose monitoring device 904 estimates the blood glucose concentration based on data collected by the glucose sensor. The glucose sensor, for example, generates data indicative of the glucose level in the medical fluid sample of the subject, and the controller estimates the blood glucose concentration based on this glucose level. The glucose monitoring device 904 includes, for example, calibration data usable by the controller to estimate the blood glucose concentration. In some examples, the calibration data are determined based on a glucose level measured from a sample of whole blood from the subject.

The hemoglobin testing system 906 is capable of measuring characteristics of hemoglobin from a medical fluid sample of the subject. The characteristics of hemoglobin include, for example, an amount of HbA1c in the medical fluid sample of the subject. The amount of HbA1c is, for example, measured from a blood sample of the subject including a population of red blood cells (RBCs). The hemoglobin testing system 906 determines a value indicative of an average HbA1c of the population of RBCs. In some examples, the medical fluid sample includes whole blood and/or plasma. The hemoglobin testing system 906 performs, for example, a high performance liquid chromatography, an immunoassay, or other appropriate operation to measure characteristics of hemoglobin from the medical fluid sample.

In some cases, the computing system 902, the glucose monitoring device 904, and the hemoglobin testing system 906 are part of a communication network. The data are transmitted between the computing system 902, the glucose monitoring device 904, and the hemoglobin testing system 906 through wired and/or wireless connections. In some cases, one or more of the computing system 902, the glucose monitoring device 904, and the hemoglobin testing system 906 includes a wireless communications system to enable wireless communication of data.

In some implementations, data are communicated between the computing system 902, the glucose monitoring device 904, and/or the hemoglobin testing system 906 through input facilitated by a user, e.g., a health care provider. The user operates a user input device to provide the data to the computing system 902, the glucose monitoring device 904, and/or the hemoglobin testing system 906. In one specific example, the glucose monitoring device 904 provides an output indicative of data, and the user manually operates the user input device to provide the data to the computing system 902.

While described as a separate computing system, the computing system 902, in some implementations, corresponds to a computing system that is part of the glucose monitoring device 904 and/or the hemoglobin testing system 906. The computing system 902 is, for example, a computing system housed within the glucose monitoring device 904.

Example Process

Figure 10:
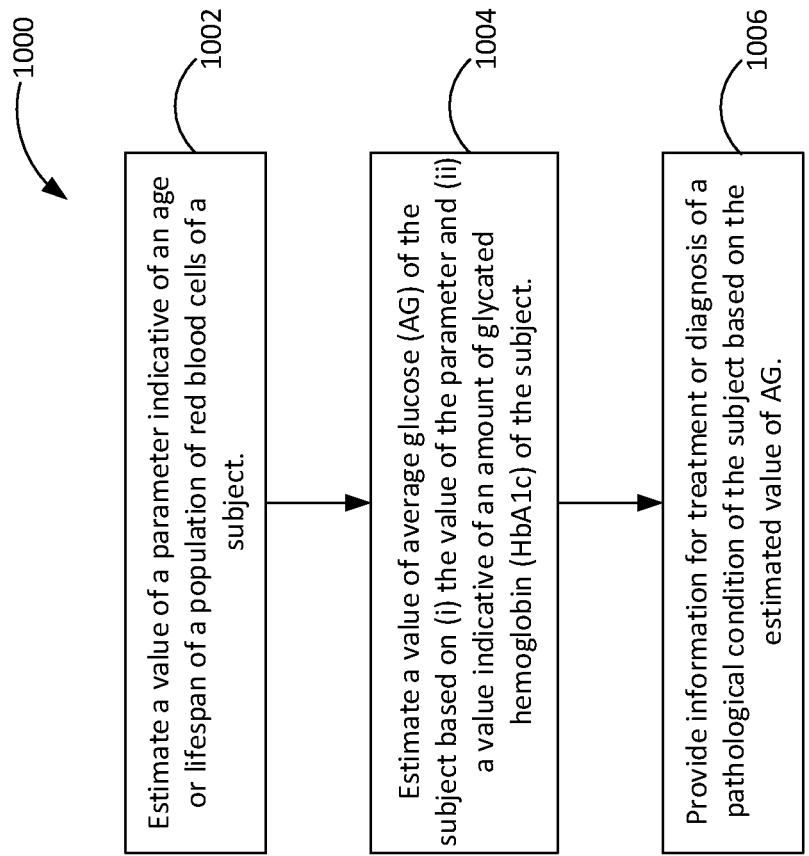
FIG. 10 is a flowchart of a process to provide information for treatment or diagnosis of a pathological condition.

FIG. 10 is a flowchart of a process 1000 that can improve the accuracy of AG estimates in accordance to the technology described herein. The process 1000 is, for example, performed by the computing system 902 to provide information for diagnosis or treatment of the subject. The information is provided to, for example, a user output device to inform a health care provider of treatment and diagnostic alternatives for the subject.

At an operation 1002, a value of a parameter indicative of an age or lifespan of a population of RBCs of a subject is estimated. The parameter is indicative of an average red blood cell age ($M_{RBC}$). In some implementations, the parameter is indicative of a half-life of a red blood cell (RBC) population or an average RBC lifespan. The parameter can vary between different subjects and serves as an indicator of non-glycemic or glucose-independent factors that cause variation in HbA1c of the subject. The parameter is a subject-specific parameter having a value that varies for different subjects. The parameter is estimated to improve the accuracy of estimates of the amount of HbA1c of the subject.

In some examples, the value of the parameter is estimated from a biomarker indicative of the age or lifespan of the population RBCs. An amount or a characteristic of the biomarker is measured, and the value of the parameter is estimated based on the amount or the characteristic of the biomarker. In some cases, the value of the parameter is estimated based on multiple biomarkers.

In one example, the biomarkers are an amount of HbA1c of the subject and a blood glucose concentration of the subject. The value of the parameter is estimated based on a value indicative of the amount of HbA1c of the subject and/or the value indicative of blood glucose concentration of the subject. The HbA1c amount and the blood glucose concentration measured for use during the operation 1002 represent baseline data for calibrating a future estimation of a value indicative of the blood glucose concentration.

The parameter serves as a basis for the future estimation of the value indicative of the blood glucose concentration, thereby avoiding the need for future direct measurements of blood glucose concentration to obtain the value indicative of the blood glucose concentration. The value indicative of the HbA1c can be directly measured to provide data for estimating the value indicative of the blood glucose concentration. As described herein, in alternative implementations, the parameter can also be used to estimate future values of HbA1c from a value indicative of the blood glucose concentration. The value indicative of the blood glucose concentration can be directly measured while the value indicative of the HbA1c is estimated from the direct measurement of the blood glucose concentration.

The value indicative of the amount of HbA1c is measured using the hemoglobin testing system 906. The value indicative of blood glucose concentration of the subject is measured using the glucose monitoring device 904. In this regard, in some cases, during the process 1000, data representing these values are received, e.g., by the computing system 902.

The value indicative of blood glucose concentration represents, for example, an average glucose (AG). In some examples, this value represents an average, a weighted average, or other statistical quantity representative of multiple values of blood glucose concentration measured. As a result, multiple values of blood glucose concentration serve as the basis for estimating the parameter. The process to measure the HbA1c amount using hemoglobin testing system 906 can be a relatively less invasive process than the process to measure the blood glucose concentration.

In some cases, the value indicative of the amount of HbA1c is estimated based on multiple values of HbA1c of the subject measured after the time period in which the value of the blood glucose concentration is measured. The value of the amount of HbA1c is indicative of an average of the multiple measurements. In some cases, the value indicative of the amount of HbA1c is an average of HbA1c over a range of ages, e.g., between an age of 0 and a lifespan of RBCs in the population of RBCs.

The value of the amount of HbA1c is measured after a time period in which value indicative of the blood glucose concentration is also measured. In some cases, the value indicative of the blood glucose concentration is estimated based on data collected by the glucose monitoring device 904 over the duration of the time period. The duration of the time period is at least, for example, 7 days to 120 months, e.g., 7 days to 14 days, 14 days to 28 days, 1 month to 2 months, etc. In one example, the duration of the time period corresponds to a maximum expected lifespan of an RBC in the population of RBCs. The data represent multiple measurements of blood glucose concentration collected by the glucose monitoring device 904 during the time period.

The time at which the value indicative of the HbA1c is measured is after the time period during which the data are collected. The HbA1c measurement time is within, for example, 0 days to 30 days after the blood glucose concentration data collection time period. The HbA1c measurement time is preferably within 7 days after the blood glucose concentration data collection time period.

In some examples, the parameter is determined based on a weighted average of multiple values indicative of blood glucose concentration of the subject. Because the amount of HbA1c at a given time is influenced by previous values of blood glucose concentration, the weighted average accounts for relative times at which the blood glucose concentration is measured. The weighted average is determined based on times at which the values indicative of blood glucose concentration are measured relative to a time at which the value indicative of the amount of HbA1c is measured. The blood glucose concentration measurement times that are closer to the HbA1c measurement time are weighted more heavily than the blood glucose concentration measurement times that are farther from the HbA1c measurement time.

In one example, the weighted average is determined using the following expression:

$$AG = \frac{1}{2 \cdot M_{RBC}} \int_0^{2 \cdot M_{RBC}} \left( \frac{1}{t} \int_{-t}^0 \text{glucose}(\tau) d\tau \right) dt$$

where $M_{RBC}$ is the average red blood cell age and glucose($\tau$) is the blood glucose concentration measured at a given time $\tau$, and $2 \cdot M_{RBC}$ represents the period of time over which the blood glucose concentration measurements are averaged. In this regard, the blood glucose concentration measurement times are weighted over a time period that corresponds to an expected lifespan of RBCs in the population of RBCs. In some cases, the expected lifespan is between 1.8 to 2.2 times the average age of the RBCs ($M_{RBC}$). In some implementations, if the blood glucose concentration measurements are taken over a time period less than $2 \cdot M_{RBC}$, the blood glucose concentration measurements are averaged over this time period instead of over $2 \cdot M_{RBC}$.

At an operation 1004, a value of AG of the subject is estimated. The value of AG is estimated based on the value of the parameter estimated at the operation 1002. The value of AG is also estimated based on a value indicative of an amount of HbA1c of the subject. This value indicative of the amount of HbA1c is measured using the hemoglobin testing system 906.

Using the earlier measured first value indicative the amount of HbA1c and the earlier measured value indicative of the blood glucose concentration, an additional value indicative of blood glucose concentration is estimated during the operation 1004. The earlier measured values provide a basis for predicting a future value of blood glucose concentration based on a future value indicative of the amount of HbA1c. As described herein, the earlier measured values serve as baseline data for calibrating the estimation of the additional value indicative of the blood glucose concentration. This baseline data can improve accuracy of this estimation as well as avoid direct measurement of the additional value indicative of the blood glucose concentration.

The value indicative of the amount of HbA1c used to determine the estimated value of AG during the operation 1004 is a value distinct from the value indicative of the amount of HbA1c used to determine the parameter. In this regard, the value indicative of the amount of HbA1c used to determine the parameter is a first value, and the value indicative of the amount of HbA1c used to determine the estimated value of AG is a second value. The first value corresponds to the baseline data for calibrating the estimate of the value of AG. The first value is measured at a first time before a second time at which the second value is measured. The first time period is, for example, 0 days to 1 year before the second time period, e.g., between 0 days and 7 days, 1 day and 1 month, 1 day and 2 months, 1 month and 3 months, 1 month and 1 year, etc., before the second time period.

In some implementations, the process 1000 further includes an operation in which a subject-specific relationship between values indicative of blood glucose concentration and values indicative of HbA1c for the subject is determined. The subject-specific relationship accounts for glycemic-driven variation in HbA1c amount as well as non-glycemic-driven variation in HbA1c amount. In particular, the subject-specific relationship indicates a variation in HbA1c amount as blood glucose concentration varies, and indicates further variation in HbA1c amount as a non-glycemic quantity varies. The parameter determined during the operation 1002 represents this non-glycemic quantity. The subject-specific relationship is defined by the parameter. The parameter is a subject-specific parameter that is determined based on specific measured characteristics of the subject, e.g., the blood glucose concentration or the HbA1c amount of the subject. The value of the AG of is estimated based on the subject-specific relationship.

In some examples, the subject-specific relationship is defined by a value of a glycation rate constant and/or a value of a reticulocyte HbA1c amount. In one example, the subject-specific relationship is a linear relationship between the values indicative of AG and the values indicative of the amount of HbA1c. The subject-specific relationship is, for example, $$HbA1c = HbA1c(0) + [1 - HbA1c(0)] \cdot k_g \cdot M_{RBC} \cdot AG$$

where $k_g$ is the glycation rate constant, HbA1c(0) is the value of the reticulocyte HbA1c amount, and $M_{RBC}$ is the average RBC age. The value of the reticulocyte HbA1c amount represents a y-intercept of the subject-specific relationship. The product of [1−HbA1c(0)], the glycation rate constant, and $M_{RBC}$ is the slope of the subject-specific relationship.

In another example, the subject-specific relationship is a non-linear relationship between the values indicative of AG and the values indicative of the amount of HbA1c. The subject-specific relationship is, for example, $$HbA1c = \frac{1}{2 \cdot \widetilde{M}_{RBC}} \int_0^{\cdot} \left[ HbA1c(0) + AG \cdot \frac{k_g}{tHb} \cdot \int_0^t (tHb - gHb(\tau))d\tau \right] dt$$

where $\widetilde{M}_{RBC}$ is an estimated average red blood cell age, HbA1c(0) is the value of the reticulocyte HbA1c amount, AG is an average glucose of the subject, $k_g$ is the glycation rate constant, tHb is the concentration of total hemoglobin in a red blood cell (RBC), and gHb(τ) is the glycated hemoglobin at an age τ. The subject-specific relationship assumes a uniform distribution of RBC ages between 0 and $2 \cdot \widehat{M_{RBC}}$. In other implementations, other distributions of RBC age is assumed, e.g., a normal distribution, etc. Using this subject-specific relationship, the value of AG of the subject is, for example, numerically estimated.

At an operation 1006, information for treatment or diagnosis of a pathological condition of the subject is provided. The information is provided based on the estimated value of AG. The estimate value of AG serves as an indicator of a presence or an absence of the pathological condition and also serves as an indicator of an appropriate treatment course to be administered to the subject. The pathological condition corresponds to, for example, a metabolic condition, a hyperglycemia condition, a hypoglycemia condition, a blood disorder, diabetes, anemia, iron deficiency, etc. The pathological condition is, for example, a blood sugar condition such as hyperglycemia or hypoglycemia.

If the operation 1006 is performed by the computing system 902, the computing system 902 provides the information in a manner that enables a health care provider to administer the appropriate treatment course or to make the appropriate diagnosis. In some cases, the information is provided to a user terminal connected to the computing system 902. The information includes user interface data that causes the user terminal to present the estimated value of AG to the health care provider. Alternatively or additionally, the computing system 902 determines the appropriate diagnosis and/or the appropriate treatment course based on the estimated value of AG, and the information causes the user terminal to present the appropriate diagnosis and/or the appropriate treatment course.

In another example, the computing system 902 provides the information directly to a computing device on the subject, e.g., a computing device on the glucose monitoring device 904, a smartphone, a tablet, or other device carried by the subject. The information causes the computing device to present the estimated value of AG or the appropriate treatment course for the subject. The subject can self-administer medication, e.g., to treat a hyperglycemia condition, based on the estimated value of AG or can undergo the appropriate treatment course. In some cases, a diagnosis of the hyperglycemia condition.

In some implementations, the process 1000 further includes an operation in which a diagnostic threshold for the pathological condition is determined based on the parameter and the estimated value of AG. The diagnostic threshold corresponds to a threshold value for an amount of HbA1c or a threshold value for blood glucose concentration. In one example, the information provided in operation 1006 includes information indicative of a diagnosis of the pathological condition when the value indicative of the amount of HbA1c, e.g., the second value indicative of the amount of HbA1c, is above the diagnostic threshold. In this regard, the diagnostic threshold is a subject-specific diagnostic threshold.

In some cases, the information includes data representing an amount of medication to administer to the subject. The medication is, for example, insulin, isophane insulin, insulin analogs, etc. In one example, the information includes the estimated value of AG, and a health care provider determines the amount of medication to administer based on the estimated value of AG. Rather than determining the amount of medication to administer based on a value indicative of an amount of HbA1c alone, the amount of medication to administer is determined based on both a value indicative an amount of HbA1c and the value of the parameter.

In some examples, rather than determining the value of AG at operation 1004, the value for $M_{RBC}$ is used to guide treatment of a blood disorder, such as anemia. A treatment for a patient who is being treated with erythropoiesis stimulating agents (ESA), e.g., a dose of the ESA, is adjusted based on estimations of Masc. In cases where the pathological condition is anemia, the healthcare professional can determine an optimization of ESA or iron supplementation therapy. In some examples, if a patient is being treated, and the estimated value of Maw decreases, then the treatment is likely to be working, and the dose of the ESA or iron is maintained or reduced. If $M_{RBC}$ is not changing or is increasing, the dose is increased, or another treatment can be attempted.

In some examples, a disease-appropriate treatment, e.g., a dose of a medication to treat anemia, for a patient being treated for a disease for which anemia is a marker of poor prognosis is intensified if $M_{RBC}$ is not decreasing. The treatment is reduced if Maw is decreasing. The treatment can be maintained, increased in dose, or decreased in dose based on the estimated $M_{RBC}$.

In some examples, the $M_{RBC}$ can be useful to guide training for improved athletic performance. If a training program causes MRBC to decrease, it may be inferred that the training program is leading to an increase in RBC mass as desired. The training program can be maintained, increased in intensity, or decreased in intensity based on the estimated $M_{RBC}$.

In one example, the process 1000 is performed by a computing system, e.g., the computing system 902, of a medical facility. The computing system receives the data indicative of physiological measurements of the subject, e.g., the blood glucose concentration measurements and/or the HbA1c measurements. The computing system stores these data as a longitudinal medical record for the subject in the computing system. When the longitudinal medical record is accessed by a health care provider through the user terminal, the computing system provides the information for treatment or diagnosis of the subject of the pathological condition to the user terminal. In particular, the computing system causes the user terminal to indicate to the health care provider the estimated value of AG or to indicate a recommended diagnosis or treatment course.

Example Computing System

Figure 11:
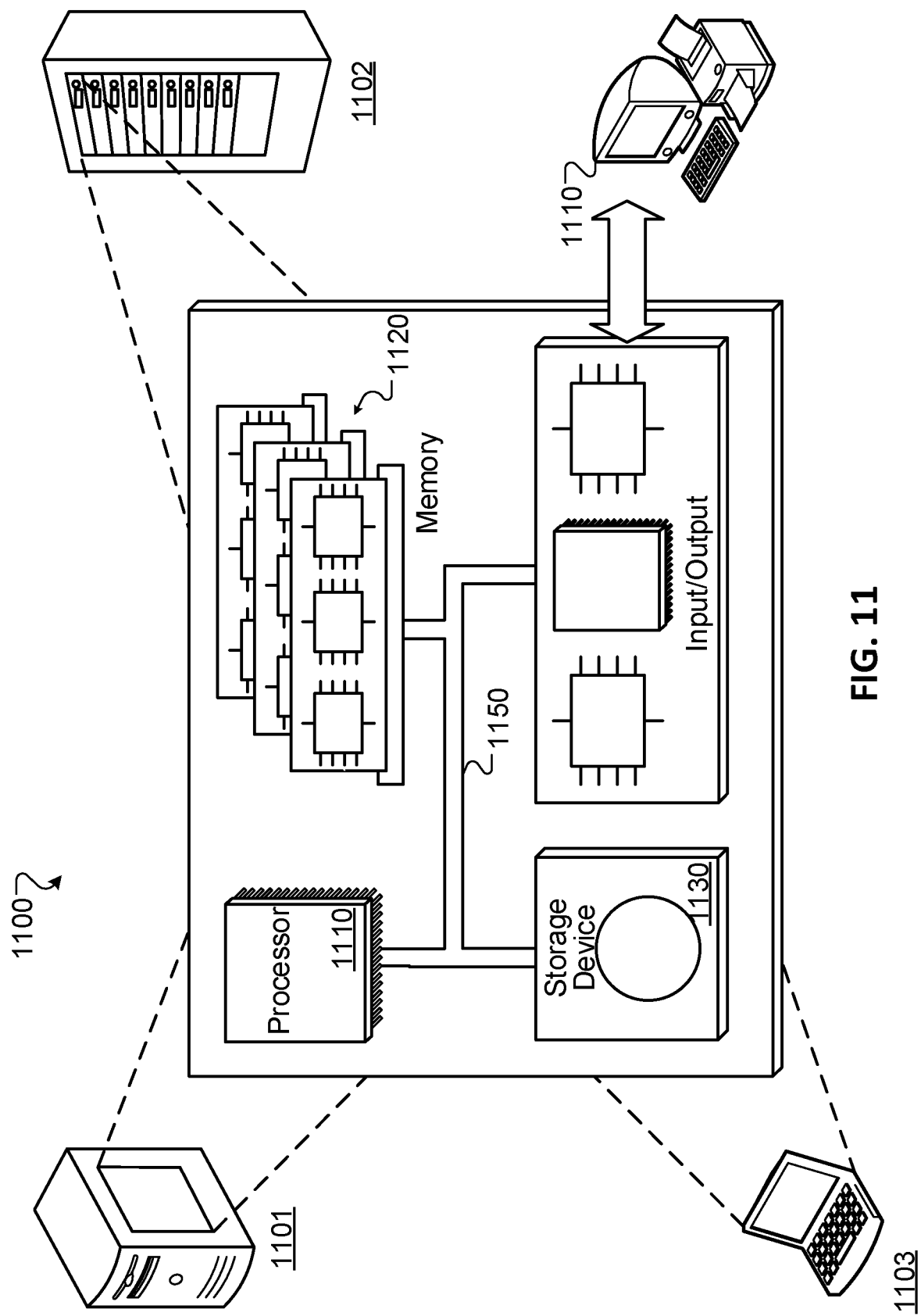
FIG. 11 is a schematic drawing of a computing system.

FIG. 11 is a schematic diagram of an example of a computer system 1100 that can be used for operations described in association with any of the computer-implemented methods and processes described herein. The system 1100 is intended to represent various forms of digital computers, including, e.g., laptops, desktops, workstations, personal digital assistants, servers, blade servers, mainframes, and other appropriate computers. In this regard, the computer system 802, for example, includes features similar to the features described herein with respect to the computer system 1100. In some cases, other computing systems and devices described herein, such as the computing system of the hemoglobin testing system 806, the controller of the glucose monitoring device 804, and other computing systems and devices described herein, include features described with respect to the computer system 1100. The system 1100 can be incorporated in various computing devices such as a desktop computer 1101, server 1102, and/or a laptop computer 1103.

The computer system 1100 receives data from external measurement and testing systems, stores the data, and processes the data. In some cases, as described herein, the computing system 1100 makes determinations about a treatment plan, a diagnosis plan, a training plan, or other appropriate medical procedure or recommendation for a subject associated with the data. Alternatively or additionally, the computing system 1100 provides information for making the determinations.

The computer system 1100 includes a processor 1110, a memory storage element 1120, a storage device 1130, and an input/output device 1140. Each of the components 1110, 1120, 1130, and 1140 are interconnected using a system bus 1150. The processor 1110 is capable of processing instructions for execution within the system 1100. In some implementations, the processor 1110 is a single-threaded processor. In some implementations, the processor 1110 is a multi-threaded processor. The processor 1110 is capable of processing instructions stored in the memory storage element 1120 or on the storage device 1130 to display graphical information for a user interface on the input/output device 1140.

The memory storage element 1120 stores information within the system 1100. In some implementations, the memory storage element 1120 is a computer-readable medium. The memory storage element 1120 includes, for example, volatile memory and/or non-volatile memory.

The storage device 1130 is capable of providing mass storage for the system 1100. In one implementation, the storage device 1130 is a computer-readable medium. In various different implementations, the storage device 1130 may be a floppy disk device, a hard disk device, an optical disk device, or a tape device.

The input/output device 1140 provides input/output operations for the system 1100. In some implementations, the input/output device 1140 includes a keyboard and/or pointing device. In some implementations, the input/output device 1140 includes a display unit for displaying graphical user interfaces. In some implementations, the input/output device is configured to accept verbal (e.g. spoken) inputs. The clinician, for example, provides the input by speaking into the input device.

The features described can be implemented in digital electronic circuitry, or in computer hardware, firmware, or in combinations of these. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 1110 carries out instructions related to a computer program. The processor 1110 may include hardware such as logic gates, adders, multipliers and counters. The processor 1110 may further include a separate arithmetic logic unit (ALU) that performs arithmetic and logical operations.

ALTERNATIVE IMPLEMENTATIONS

A number of implementations have been described. Nevertheless, it will be understood that various modifications may be made.

While the parameter is described as being estimated in operation 902, in some implementations, the parameter is directly measured. The value indicative of the parameter is directly measured. In one example, the value indicative of $M_{RBC}$ is directly measured.

While the process 900 is described as a process to estimate a value of AG, in some implementations, a value of an amount of HbA1c is estimated. The measurements made in operation 902 serve as baseline data for estimating both future values of HbA1c and future values of AG. If future values of AG are estimated as described in the operation 904, these future values are estimated based on future measured values of HbA1c and the baseline data in operation 902. In contrast, if future values of HbA1c are measured, these future values are estimated based on future measured values of blood glucose concentration. In particular, the value of the amount of HbA1c is estimated based on the value of the parameter and/or a value indicative of blood glucose concentration of the subject. In this regard, while the information provided at the operation 906 is described as being provided based on the estimated value of AG, in such implementations, the information is provided based on the estimated value of the amount of HbA1c.

In one example, rather than estimating the value of the AG at the operation 904, the value of HbA1c is estimated based on a measured value indicative of blood glucose concentration. The value indicative of blood glucose concentration used to estimate the value of the amount of HbA1c is a second value indicative of blood glucose concentration, and the estimated value of the amount of HbA1c is a second value of the amount of HbA1c. The value of the parameter is estimated based on a first value indicative of blood glucose concentration and a first value indicative of the amount of HbA1c. These first values correspond to baseline data for estimating the second future value indicative of the amount of HbA1c based on the second future measured value indicative of blood glucose concentration.

The first value indicative of the amount of HbA1c is measured after the first value indicative of blood glucose concentration is measured. The time at which the first value indicative of blood glucose concentration is measured and the time at which the first value of the amount of HbA1c is measured are both earlier than the time at which the second value indicative of blood glucose concentration is measured. The first value indicative of the amount of HbA1c is measured, for example, using the hemoglobin testing system 806 described herein, and the first and second values of blood glucose concentration are measured using the glucose monitoring device 804.

If the process includes an operation to determine a diagnostic threshold, the diagnostic threshold is determined based on the parameter. The diagnostic threshold is further determined based on either or both of the estimated value indicative of HbA1c and the measured value indicative of blood glucose concentration. The diagnostic threshold corresponds to a threshold value for an amount of HbA1c or a threshold value for blood glucose concentration. In one example, the information provided in operation 906 includes information indicative of a diagnosis of the pathological condition when the value indicative of the amount of HbA1c, e.g., the second estimated value indicative of the amount of HbA1c, is above the diagnostic threshold. In this regard, the diagnostic threshold is a subject-specific diagnostic threshold.

Accordingly, other implementations are within the scope of the claims and the examples in the Examples section and described herein elsewhere.

EXAMPLES

Certain aspects are further described in the following examples, which do not limit the scope of the claims.

Example 1: Method for Estimating AG from HbA1c

In the examples below, an accurate method for estimating a value for AG from a value for HbA1c was developed by adjusting for inter-patient variation in non-glycemic factors affecting HbA1c. An example derivation of this method is described with respect to Examples 1A to 1C. As described with respect to Example 1D, reproducibility of the results was demonstrated by analyzing four independent sets of patients and finding consistent improvement in the accuracy of estimated AG using the patient-specific model. Example 1E presents an analysis of error.

Example 1A: Derivation of a Model of Hemoglobin Glycation and RBC Kinetics

The process of HbA1c formation inside a single RBC can be described by the irreversible chemical reaction of hemoglobin (Hb) with glucose to form glycated hemoglobin (gHb) with rate $k_g$:

$$Hb + Glucose \xrightarrow{k_g} gHb \tag{1}$$

The rate of change in gHb in Equation (1) can be modeled as a differential equation:

$$\frac{d}{dt}gHb(t) = k_g \cdot AG \cdot (tHb - gHb(t)) \tag{2}$$

In Equation (2), tHb is the concentration of total hemoglobin in the RBC. The variable t is the time for the glycation reaction and is equivalent to the RBC's age. The glycation kinetics can describe glycation in a single RBC (11, 12, 14, 15). Equation (2) can be solved analytically and scaled by tHb to yield HbA1c in an RBC of age t:

$$HbA1c(t) = \frac{gHb(t)}{tHb} = 1 - e^{(-k_g \cdot AG \cdot t)} + \frac{gHb(0)}{tHb}e^{(-k_g \cdot AG \cdot t)} \tag{3}$$

Equation (3) represents a patient-specific relationship between values of HbA1c amount and values of blood glucose concentration, e.g., average glucose, and can be used to estimate values of HbA1c amount or to estimate values of blood glucose concentration.

In Equation (3), AG instead of a time-varying glucose is used to simplify the analysis for the derivation of the patient-specific model described herein. In some implementations, a time-varying blood glucose concentration is used. The effects of time-varying glucose on the patient-specific model is described in Example 1D. gHb(0) is the concentration of glycated hemoglobin in the RBC when it is a reticulocyte and has just entered the circulation.

Because $e^x \approx 1+x$ when x is small, Equation (3) can be approximated with a linear function. By linearizing the exponential in this way, it can be averaged over the roughly uniformly-distributed ages of RBCs (t) in a patient's circulation (3, 4, 16) to provide the clinically measured HbA1c:

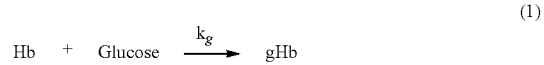

$$HbA1c = HbA1c(0) + [1 - HbA1c(0)] \cdot k_g \cdot M_{RBC} \cdot AG \tag{4}$$

Equation (4) also represents a patient-specific relationship between values of HbA1c amount and values of blood glucose concentration, e.g., average glucose, and can be used to estimate values of HbA1c amount or to estimate values of blood glucose concentration. In Equation (4), HbA1c(0) is the y-intercept of the linear relationship between HbA1c and AG, and $[1-HbA1c(0)] \cdot k_g \cdot M_{RBC}$ is the slope of the linear relationship. Example 5 herein describes a derivation of the AG-HbA1c linear regression from the physiological model of glycation.

Figure 1:
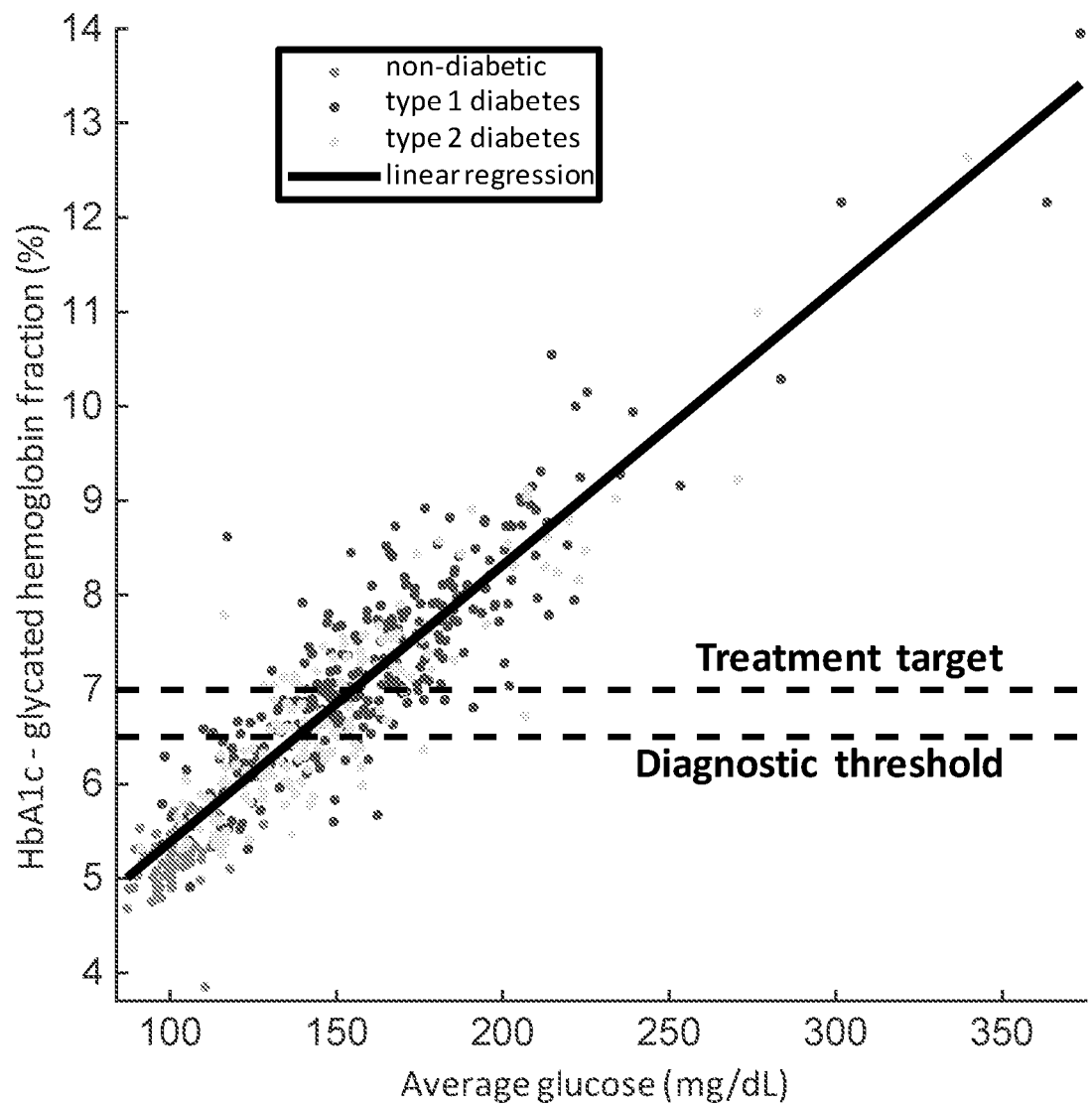
FIG. 1 is a plot of data points of average glucose and glycated hemoglobin fraction with a linear relationship between the average glucose and the glycated hemoglobin fraction overlaid on the plot. The data points represent data collected from non-diabetic patients, patients having type 1 diabetes, and patients having type 2 diabetes.

FIG. 1 shows a linear relationship between AG and HbA1c. The linear regression line shown in FIG. 1 is computed based on all of the data points shown in FIG. 1. The treatment target line refers to the target HbA1c value for patients when the patients are being treated for diabetes, hyperglycemia, etc. The diagnostic threshold line refers to the threshold HbA1c value to diagnose a patient with diabetes. The diagnostic threshold for a value of HbA1c is, for example, about 6.5%. The treatment target for a patient with diabetes is a value of HbA1c of, for example, about 7%.

The linear relationship between Ag and HbA1c has been reported in several studies such as the A1c-Derived Average Glucose (ADAG) study described in Reference (1). Direct estimation of AG based solely on HbA1c may be inaccurate, in part because of the imprecision and inaccuracies of the component measurements. There can be significant glucose-independent variation. The glucose-independent variation can include a linear relationship between $M_{RBC}$ and HbA1c. Regardless of the cause, an AG of 150 mg/dL may be associated with HbA1c anywhere between 5.5% and 8.0%, and HbA1c of 6.5% may reflect AG anywhere between 125 mg/dL and 175 mg/dL.

Example 1B: Analysis of Patient-Specific Differences in the AG-HbA1c Linear Relationship The scatter of data points away from the regression line as shown in FIG. 1 represents patient-specific deviation from the regression model presented in Equation (4) in terms of the intercept or the slope. FIG. 2A-2D illustrate the different effects the intercept variation and the slope variation have on the HbA1c conditional variance.

Figure 2A:
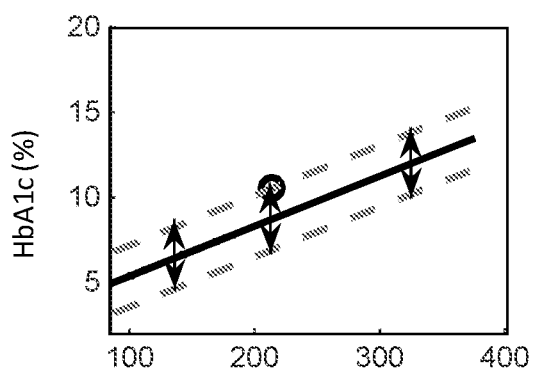
FIGS. 2A and 2B are graphs of a linear relationship between average glucose and glycated hemoglobin fraction with representations of intercept variation and slope variation, respectively, overlaid on the graphs.

Analysis of HbA1c variance as a function of AG suggested that inter-patient variation in the slope rather than the intercept is a more significant cause of glucose-independent variation in HbA1c. The amount of variation in HbA1c in FIG. 1 was different at different AG levels, with apparently less variation in HbA1c at lower AG. As shown in FIGS. 2A and 2C, inter-patient variation in slope had a different effect from variation in intercept shown in FIGS. 2B and 2D. This relationship was analyzed by calculating the HbA1c variance within 10 mg/dL intervals of AG.

The amount of variation in HbA1c in FIG. 1 increased at higher AG levels and decreased at lower AG levels. The relationship between HbA1c variance and AG was analyzed by calculating the HbA1c variance in the ADAG data conditioned on AG. This conditional variance calculation is similar to conditional expectation calculations. Both of these calculations involve averaging over all measurements that have corresponding AG levels within predetermined intervals, e.g., of 10 mg/dL in this case. Instead of averaging HbA1c itself as in conditional expectation, the squared deviation of the HbA1c measurements from the mean are averaged: $(HbA1c - \mathbb{E}\{HbA1c\})^2$.

Figure 2B:
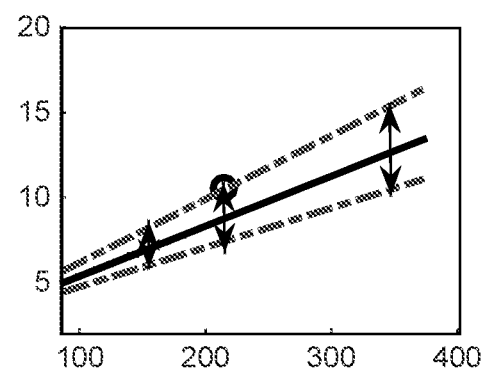
Figure 2C:
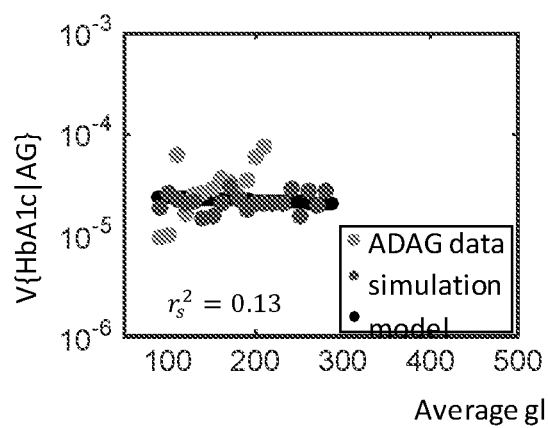
FIGS. 2C and 2D are plots of variation in the glycated hemoglobin fraction caused by the intercept variation and the slope variation shown in FIGS. 2A and 2B, respectively.
Figure 2D:
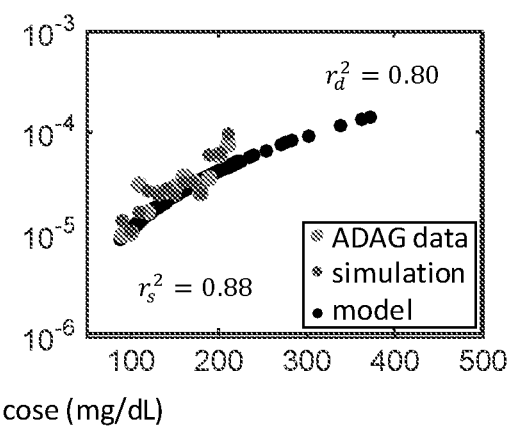

Referring to FIGS. 2C and 2D, $r_d^2$ refers to the rank correlation coefficient for the raw ADAG data shown as red dots in both FIGS. 2C and 2D. This value of this coefficient was the same in both FIGS. 2C and 2D because $r_d^2$ was independent of a model of the source of variation. In FIG. 2C, $r_s^2$ refers to the correlation for the blue dots in FIG. 2C, which represent the simulated effect of inter-patient differences in intercept on variance in AG. In FIG. 2D, $r_s^2$ refers to the correlation for the blue dots in FIG. 2D, which represent the simulated effect of inter-patient differences in slope on variance in AG.

As shown in FIG. 2A, the possibility of significant inter-individual variability in the intercept was assessed. FIG. 2C illustrates a simulation of the effect of increasing variability in HbA1c(0) or reticulocyte HbA1c amount when the slope was fixed. This hypothesized model of inter-patient differences in intercept (black line in FIG. 2C) generated data (blue points in FIG. 2C) that did not agree with the experimental data (red dots in FIG. 2C). The value of the correlation coefficient between these data was $r_1^2 = -0.05$. Based on these results, inter-patient differences in reticulocyte HbA1c were determined to be unlikely to be responsible for glucose-independent variation seen in HbA1c.

FIG. 2B illustrates the expected effect of inter-patient variation in the slope of the regression line, the slope being the product of the terms $[1-HbA1c(0)]$, $k_g$, and $M_{RBC}$. As shown in FIG. 2D, the correlation between the simulated and actual data in this case was high. Because the model was linear, the variance was analytically calculated around the regression line, as illustrated by Equation (5) below and represented as black dotted lines in FIGS. 2C and 2D. The correlation between the conditional variance and AG calculated from simulated HbA1c and the ADAG data was $r_s^2 = 0.94$. Similarly, the correlation in the ADAG data was $r_d^2 = 0.65$ (FIG. 2D). Note that in the ADAG data, out of 507 samples, there were 2 outliers both with AG in the range of 110-120 mg/dL, creating a single bin for the calculation of conditional variance. In FIG. 2D, these two samples were removed, increasing $r_d^2$ to 0.80. Based on these results, it was determined to be more likely that inter-individual variation in the regression slope, not inter-individual variation in the regression intercept, was responsible for variation observed in the AG-HbA1c relationship.

In the variance calculations herein, conditional expectation was taken with respect to the RBC age across the population of RBCs in one patient's circulation, as well as with respect to the $M_{RBC}$ for an individual patient across the population of individuals. The initial glycation fraction $$\frac{gHb(0)}{tHb}$$

was assumed to be a random variable. To simplify the expression, the glycation rate was treated as a constant.

$$V\{HbA1c \mid AG\} = V\left\{\frac{gHb(0)}{tHb}\right\} \cdot [1 - 2E\{M_{RBC}\} \cdot k_g \cdot AG] + \quad (5)$$
$$AG^2 \cdot k_g^2 \cdot E\{M_{RBC}\}^2 \cdot V\left\{\frac{gHb(0)}{tHb}\right\} +$$
$$E\left\{\frac{gHb(0)}{tHb}\right\}^2 \cdot V\{M_{RBC}\} + V\left\{\frac{gHb(0)}{tHb}\right\} \cdot V\{M_{RBC}\}$$

The contribution of increased variability in the reticulocyte HbA1c had the approximate effect of an 'additive noise' on the total variance, because in terms of numerical values, it had little dependence on AG. In considering the theoretical case of no variability in $M_{RBC}$, a negative slope emerged as seen in FIG. 2C, contradicting the empirical data and suggesting that $M_{RBC}$ can account for variation between the AG value and the HbA1c value.

Example 1C: Measuring Variation in $M_{RBC}$

As shown in Example 1B, inter-patient variation in the slope explained a significant portion of the non-glycemic variation in HbA1c. The slope is equal to θ=[1−HbA1c(0)]·$k_g$·$M_{RBC}$. The first component of the slope is ([1−HbA1c(0)]), which as discussed above, varies too little overall (~0.994−1.00) to be a significant cause of glucose-independent variation in HbA1c. The second component ($k_g$) did not appear to vary between patients (21). The third component ($M_{RBC}$) had a mean of about 58 days and a standard deviation of 4.5-6.5 days. The coefficient of variation $$\left[ CV(M_{RBC}) = \frac{std(M_{RBC})}{mean(M_{RBC})} \right]$$

was thus between 7.8% and 11.2% (3, 4).

In this example, a patient-specific corrected slope $$\hat{\theta} = \frac{HbA1c - HbA1c(0)}{AG}$$

was calculated at the time of a specific HbA1c measurement using AG determined from large intra-patient CGM data sets. The symbol $\hat{\theta}$ is used to represent an estimate of the true patient-specific slope θ. AG was calculated from CGM data using a weighted average of individual glucose measurements. The weighted average was used because glucose levels in the blood immediately prior to the HbA1c measurement influence the glycation levels in RBCs of all ages, while more distant glucose levels influence only those RBCs old enough to have been in the circulation at that time (22).

The AG that determines HbA1c was a weighted average of glucose levels prior to the HbA1c measurement (22). As discussed above, the clinically measured HbA1c was an average of single-RBC HbA1c over the ages of RBCs in a patient's blood sample. The RBC ages were assumed to be uniformly distributed between 0 and 2·$M_{RBC}$. The blood glucose level on the day prior to the HbA1c measurement affected the HbA1c amount of almost every RBC in the blood sample. The blood glucose levels measured much earlier and closer to 2·$M_{RBC}$ days prior to the HbA1c measurement affected the small fraction of the oldest RBCs still in circulation. The AG from CGM for the linearized model (Equation (4)) was calculated using the following equation:

$$AG = \frac{1}{2 \cdot M_{RBC}} \int_0^{2 \cdot M_{RBC}} \left( \frac{1}{t} \int_{-t}^0 glucose(\tau) d\tau \right) dt \quad (6)$$

When full CGM data is not available, it can be more valuable to have recent CGM measurements. Defining II(t) as 1 if there is CGM data within the 5 minutes prior to t and 0 if not, the fractional coverage of CGM data can be calculated during the desired time period using a related equation:

$$Coverage = \frac{1}{2 \cdot M_{RBC}} \int_0^{2 \cdot M_{RBC}} \left( \frac{1}{t} \int_{-t}^0 II(\tau) d\tau \right) dt \quad (7)$$

As described with respect to Example 4, AG can be numerically calculated from CGM without assuming the linear approximation.

Example 1D: Experimental Validation of Methods

The patient-specific model can provide an improvement in the accuracy of AG estimates. When used to estimate AG from HbA1c, the patient-specific model's sensitivity to variation in true AG can depend on the accuracy of the input HbA1c and CGM. HbA1c can be rounded to multiples of 0.1%, meaning the model can be theoretically sensitive to changes of 2-3 mg/dL in AG. Higher resolution HbA1c measurements can increase the model's sensitivity.

In this example, four distinct patient sets were analyzed. Because CGM and HbA1c data were analyzed retrospectively, both patients and treating physicians were blinded to the future use of the patient-specific model. Enrollment criteria varied for each patient, as did any policies for blinding patients to CGM readings or for randomizing patients to CGM use.

In a first patient set, CGM data from a first patient population including 36 adult patients at Massachusetts General Hospital (MGH) were analyzed under a research protocol approved by the Partners Healthcare Institutional Review Board. CGM measurements were made with Dexcom G4 continuous glucose monitors (Dexcom, Inc.). HbA1c was measured either on a Roche COBAS instrument (Roche Diagnostics) or a BIO-RAD Variant II Turbo (BIO-RAD). 36 patients had at least one HbA1c measurement with concurrent CGM covering a period of time equivalent to the most recent 30 days prior to the HbA1c measurement. 9 of those 36 individuals had a total of 16 additional future HbA1c measurements with concurrent CGM covering a period of time equivalent to the most recent 30 days prior to the HbA1c measurement. Those 16 future HbA1c measurements were used to validate the accuracy of the model-based AG estimation.

In second, third, and fourth patient sets, data for second, third, and fourth patient populations, respectively, were made available by the Jaeb Center for Health Research, a coordinating center for multi-center clinical trials and epidemiologic research. Their studies of diabetic control reported CGM and HbA1c measurements in patients and generously included raw data, enabling us to test the patient-specific model and hypothesis in three additional independent data sets.

The second patient set comes from a study entitled "Effect of Metabolic Control at Onset of Diabetes on Progression of Type 1 Diabetes" (direcnet.jaeb.org). The purpose of this study was to investigate the impact of intensive metabolic control from the onset of diabetes on preservation of C-peptide secretion. This study was conducted between November 2008 and October 2013 and included patients aged 6-46. 30 patients had at least one HbA1c measurement with concurrent CGM covering a period of time equivalent to the most recent 45 days prior to the HbA1c measurement. 23 of those 30 individuals had a total of 79 additional future HbA1c measurements with concurrent CGM covering a period of time equivalent to the most recent 45 days prior to the HbA1c measurement. Those 79 future HbA1c measurements and corresponding CGM were used to validate the accuracy of the model-based AG estimation.

For the third patient set, the data for the third patient population came from a study entitled, "A Randomized Clinical Trial to Assess the Efficacy of Real-Time Continuous Glucose Monitoring in the Management of Type 1 Diabetes" (diabetes.jaeb.org). This study was designed to compare continuous versus intensive glucose monitoring in three age groups (>25, 15-24, 8-14) of intensively treated type 1 diabetics having high glycated hemoglobin (HbA1c)

of 7.0%-10.0%. 234 patients had at least one HbA1c measurement with concurrent CGM covering a period of time equivalent to the most recent 45 days prior to the HbA1c measurement. 155 of those 234 individuals had a total of 276 additional future HbA1c measurements with concurrent CGM covering a period of time equivalent to the most recent 45 days prior to the HbA1c measurement. Those 276 future HbA1c measurements and corresponding CGM were used to validate the accuracy of the model-based AG estimation.

For the fourth patient set, the data for the fourth patient population came from a study entitled, "A Randomized Clinical Trial to Assess the Efficacy and Safety of Real-Time Continuous Glucose Monitoring in the Management of Type 1 Diabetes in Young Children (4 to <10 Year Olds)" (direcnet.jaeb.org). This study was designed to assess the efficacy of CGM in young children (4-10 years old) in terms of tolerability, safety, and effect on quality of life with type 1 diabetes. 37 patients had at least one HbA1c measurement with concurrent CGM covering a period of time equivalent to the most recent 45 days prior to the HbA1c measurement. The AG was estimated in accordance to the methods described in Example 1C and herein elsewhere. 31 of those 37 individuals had a total of 69 additional future HbA1c measurements with concurrent CGM covering a period of time equivalent to the most recent 45 days prior to the HbA1c measurement. Those 69 future HbA1c measurements and corresponding CGM were used to validate the accuracy of the model-based AG estimation.

Based on the methods described in Example 1C, $\hat{\theta}$ was calculated for the 36 distinct patients of the first patient population. $CV(\hat{\theta})$ was found to be 10.8%, within the range of variation that can be explained entirely by inter-patient variation in $M_{RBC}$. For the 339 patients of the second, third, and fourth patient populations, $CV(\hat{\theta})$ was found to be 8.8% (30 patients), 9.4% (234 patients), and 9.9% (75 patients), respectively.

Figure 3:
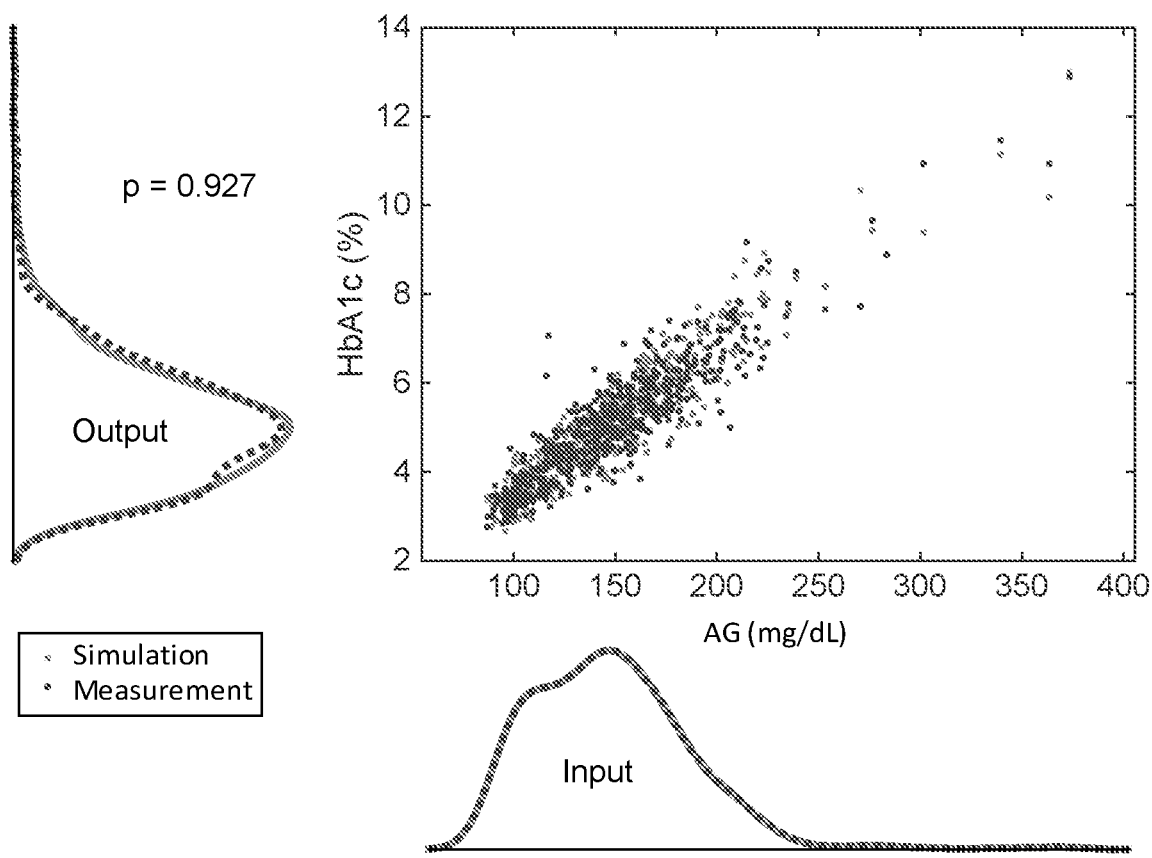
FIG. 3 is a plot of measured glycated hemoglobin fraction and average glucose values and simulated glycated hemoglobin fraction and average glucose values, the simulated values being simulated using patient-specific models.

Analysis of all four patient populations suggest that glucose-independent variation in HbA1c can be explained entirely by variation in $M_{RBC}$. FIG. 3 further shows that if [1−HbA1c(0)] and $k_g$ are constant, all measured glucose-independent variation in HbA1c in the ADAG (1) study data can be accounted for by simulating variation in $M_{RBC}$ with magnitude equivalent to that previously measured (3, 4). If either or both of the other two slope components ([1−HbA1c(0)] and $k_g$) vary significantly, they are strongly negatively correlated with $M_{RBC}$, or else $CV(\hat{\theta})$ would be much greater than $CV(M_{RBC})$. The AG values from the ADAG (1) study were used as input to Equation (4) along with constant $k_g$, constant HbA1c(0), and an $M_{RBC}$ randomly-sampled from a normal distribution with mean and standard deviation as measured in Reference (4). The medians are indistinguishable (p is the significance of a Kruskal-Wallis test of equal medians).

For the simulation in FIG. 3, the RBC lifespan was assumed to be normally distributed among different individuals with mean and variance estimated from prior publications. The simulation assumed the parametric distribution of $M_{RBC}$ was normally distributed, but the analytic calculations may not assume such a distribution. In some cases, $M_{RBC}$ has a normal distribution across individuals, while in other cases, $M_{RBC}$ has a gamma distribution. These different distributions may yield similar results. The age distribution of RBCs within an individual was assumed to be uniform, with cell ages between 0 and $2 \cdot M_{RBC}$. The glycation rate was assumed to be essentially constant (3, 21). In one example, survival of labeled RBCs was measured to yield $M_{RBC}$. AG can change across patients, especially between diabetic and non-diabetic subjects.

The fitted average parameter values (slope and intercept) were used to obtain the corresponding linear regression line. The model reconstructed the scatter of data points around the regression line adding variability in $M_{RBC}$ equivalent to that previously measured (41). In the simulations, a value of 0.001 was used for the standard deviation of reticulocyte HbA1c for the ADAG data. These values were adopted from the measurements of variation of HbA1c in reticulocytes (42). For $k_g$, a CV of 1% was allowed, though a CV of 5% with constant $M_{RBC}$ could reconstruct the variation around the regression line, as expected from the functional form of the model.

AG was assumed to be estimated with high accuracy as a result of the large number of measurements included in the average. Indeed, in the ADAG study (1) each AG value was calculated using more than 250 samples over the course of 3 months. The standard error (SE) was $$SE < \frac{SD}{\sqrt{250}} \approx \frac{SD}{15}.$$

Thus, even it the level of variability in a single glucose measurement was extremely high, for example: SD=30 (mg/dL), the resulting coefficient of variation was less than 3% for all AG values in the ADAG data. The SD for the full ADAG data set was 39 (mg/dL), and 8 (mg/dL) when restricting to the non-diabetic patients, and thus the uncertainty in AG was expected to be less than 1 (mg/dL).

The examples described herein suggest that no more than 30 days of CGM data collection is required and that statistically significant improvement in diagnosis can be made in as few as 21 days of CGM data collection. Accurate estimation of the slope based on measurements over fewer days is possible. If a patient's monthly glucose averages are stable, then the prior one month could be sufficient for calibration, and if the patient's weekly glucose averages are stable then even one week of CGM could be sufficient. The patients in the four study populations all received regular routine medical care and were generally healthy. The patient-specific model can be particularly helpful in situations where plasma glucose is likely to deviate significantly from the longer-term average reflected in HbA1c, such as optimization of treatment for a patient recently-diagnosed with diabetes (38). By controlling for patient-specific non-glycemic factors, the model can improve the clinical utility of HbA1c to provide more information regarding average glucose levels.

Analytic variation in HbA1c measurements can be ~3% (27). This variation alone can generate AG estimation errors of ~7 mg/dL. Individual CGM measurements have a reported error of about 10% (39), but because AG is an average over thousands of separate CGM measurements with frequent calibration, the expected error in AG is about 0.1%. Systematic bias in CGM measurement or calibration would reduce the accuracy of AG estimation, and advances in CGM technology to minimize bias would increase model sensitivity. Other potential sources of error beyond the model include incomplete CGM data and fluctuations in $M_{RBC}$ within an individual.

Although direct measurement of $M_{RBC}$ was not carried out, the inter-patient variation in $\widehat{M_{RBC}}$ and the intra-patient stability of $\widehat{M_{RBC}}$ are consistent with what has been shown for $M_{RBC}$ in other studies, both those directly measuring $M_{RBC}$ (3, 4) and those providing model-based estimates (24, 40). Moreover, the number of factors that might be involved in the differences between measured and calculated AG is limited, and factors such as glycation rates or intracellular pH would not be practical to measure. In the meantime, the correction factor described in Example 1 appears to be sufficient to improve the accuracy of the AG estimation from HbA1c. More generally, the clinical accuracy can be enhanced in a patient-specific manner by combining large intra-patient data sets with mechanistic dynamic models of physiology.

Example 1E: Error Analysis

Figure 5A:
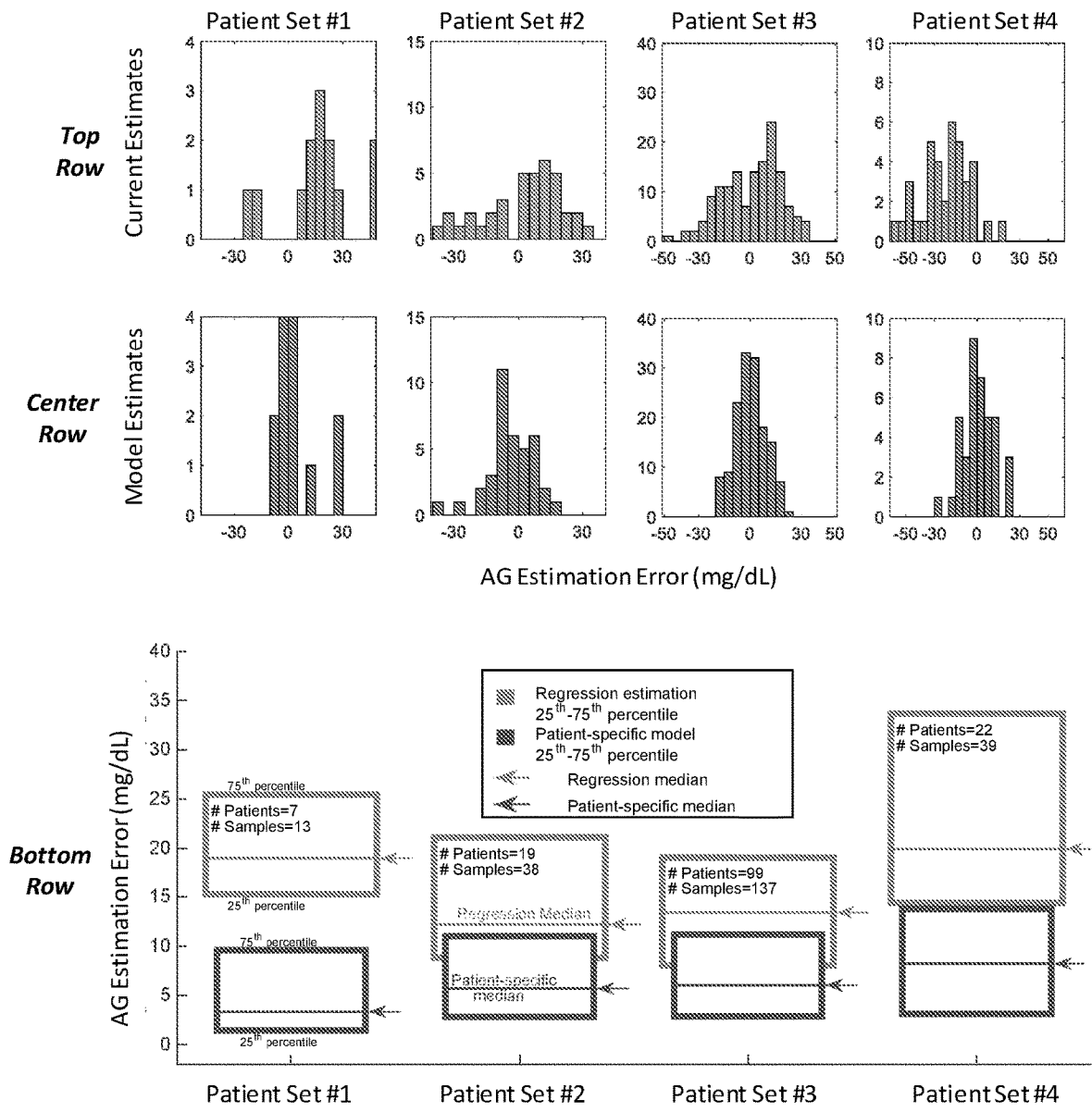
FIG. 5A includes a top row, a center row, and a bottom row with analysis of four patient sets with some data excluded, the top row showing histograms of errors in average glucose estimation of the four patient sets using a standard linear regression, the center row showing histograms of errors in average glucose estimation of the four patient sets using patient-specific models, and the bottom row showing box plots for the absolute values of errors in average glucose estimations of the four patient sets using the standard linear regression and the patient-specific models. The upper box plots in the bottom row represent the data distribution determined using the standard linear regression, and the lower box plots in the bottom row represent the data distribution determined using the patient-specific models.

FIG. 5A compares errors in predicted AG using the patient-specific model described herein and using the linear relationship described with respect to Example 1. The top row of FIG. 5A shows histograms of errors in AG estimation for 4 different sets of patients using the standard formula. The center row of FIG. 5A shows histograms of errors using model-based estimation of AG. The histograms include predictions where estimation methods differ by at least 10 mg/dL and confirm the superior accuracy of model-based AG prediction in 3 additional independent patient populations totaling more than 300 individuals. Errors for model-based predictions are significantly more tightly clustered around zero. The bottom row of FIG. 5A compares boxplots of median absolute error and shows that the model reduces error by at least 50% in each of the 4 independent sets of patients. The substantial improvement in accuracy achieved by the model is highlighted by the fact that for all 4 independent study groups, the $75^{th}$ percentile of the model-based estimation error is less than the median error for the standard regression-based prediction. The model-based estimates are superior to the standard method in all four cases with $p<0.001$.

Figure 5B:
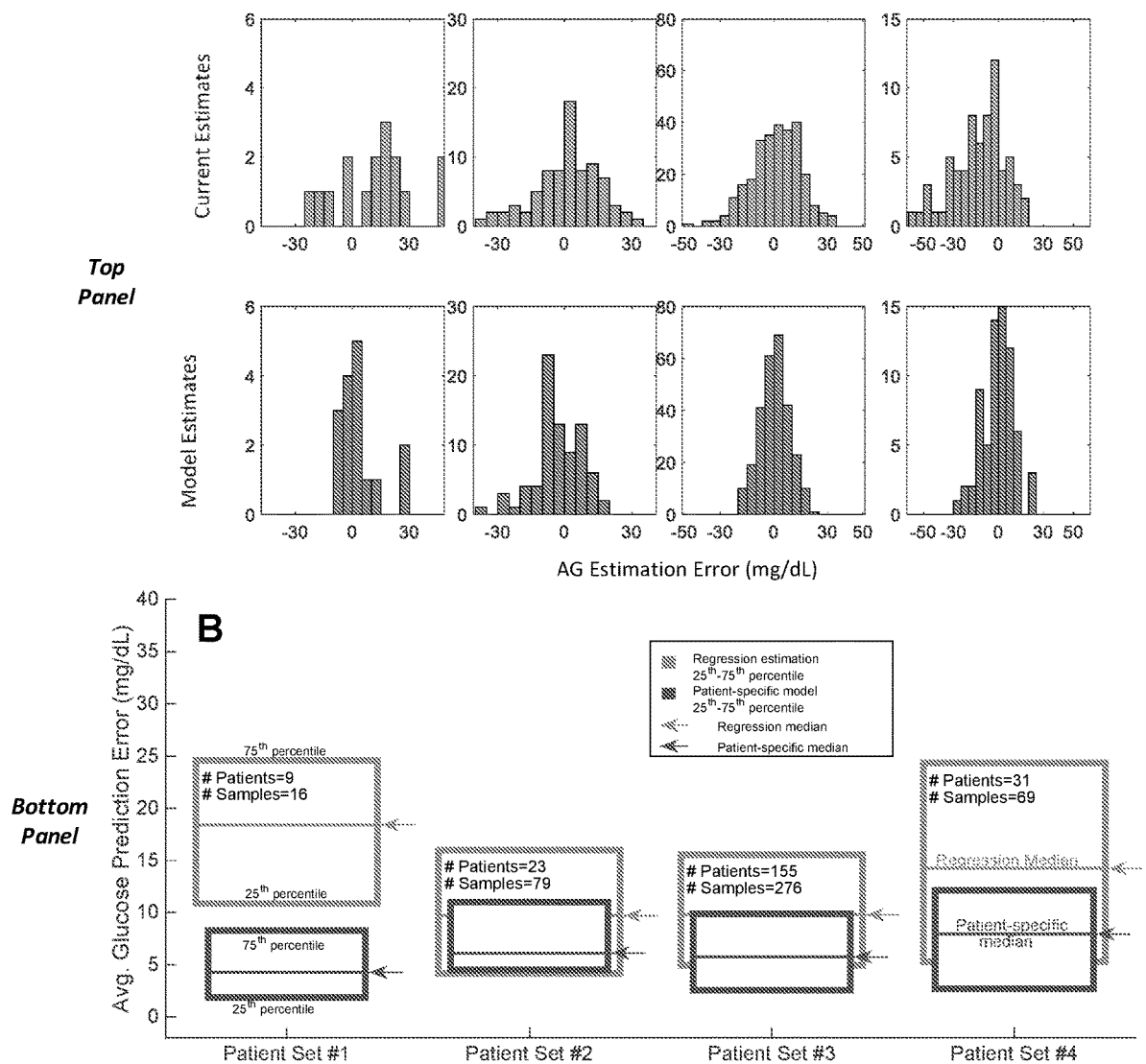
FIG. 5B includes a top row, a center row, and a bottom row with analysis of four patient sets with no data excluded, the top row showing histograms of errors in average glucose estimation of the four patient sets using a standard linear regression, the center row showing histograms of errors in average glucose estimation of the four patient sets using patient-specific models, and the bottom row showing box plots for the absolute values of errors in average glucose estimations of the four patient sets using the standard linear regression and the patient-specific models. The upper box plots in the bottom row represent the data distribution determined using the standard linear regression, and the lower box plots in the bottom row represent the data distribution determined using the patient-specific models.

FIG. 5B differs from FIG. 5A in that the histograms include all predictions even where the estimation methods agree. Model-based inference of AG from HbA1c reduces estimation errors by about 50%. The top row of FIG. 5B shows histograms of errors in AG estimation for 4 different sets of patients using the standard regression-based formula. The second row of FIG. 5B shows histograms of errors using model-based estimation of AG. Median absolute error and 75th percentile of the absolute error are listed. Errors for model-based predictions are significantly more tightly clustered around zero for all four patient populations. As shown in the bottom row of FIG. 5B, 75th percentiles for model-based errors are smaller in all cases and are smaller than the standard approach's median absolute errors in two cases.

Figure 6:
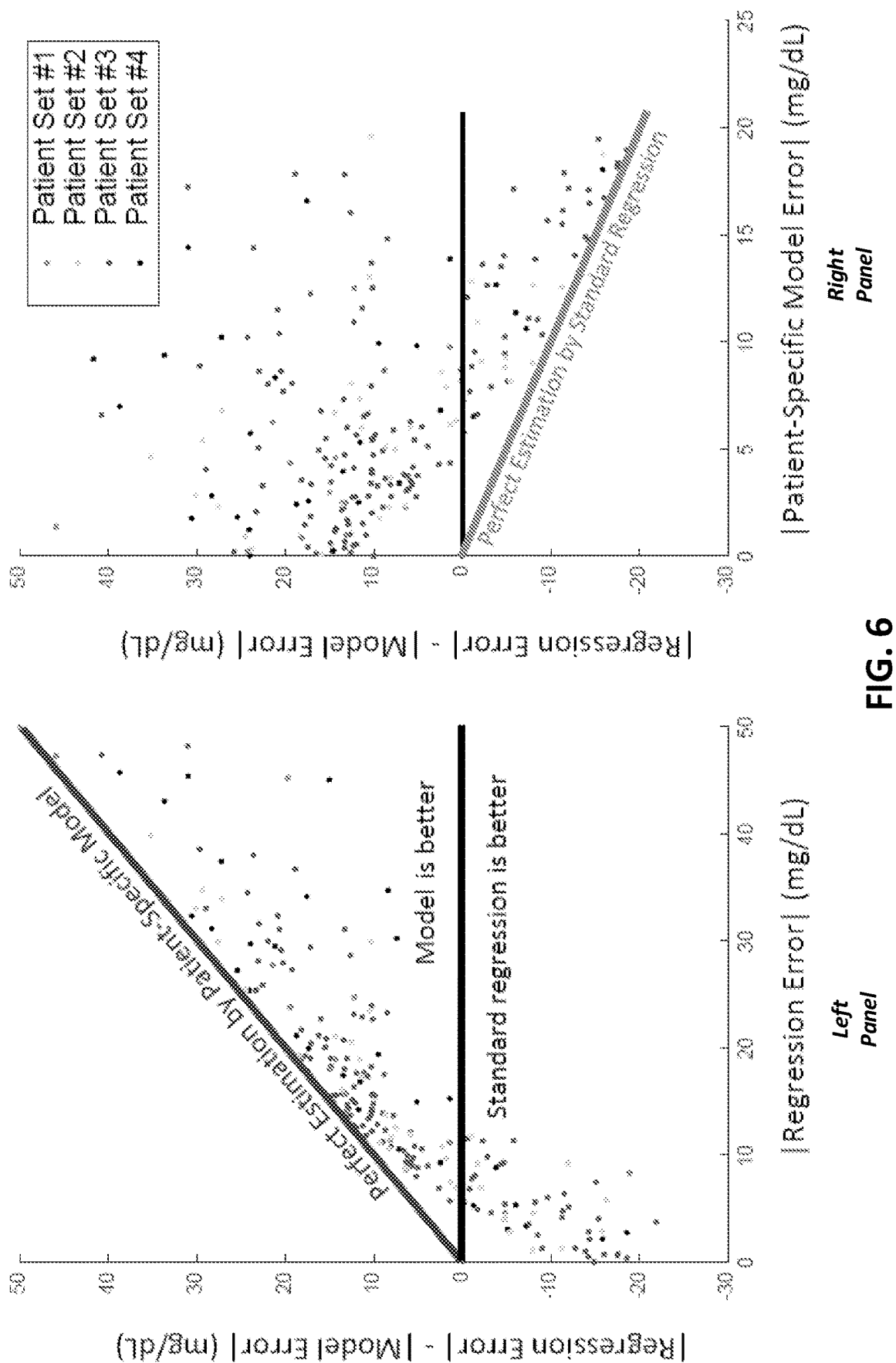
FIG. 6 includes a left panel and a right panel, the left panel shows relative errors of patient-specific model average glucose estimates as a function of errors of standard linear regression average glucose estimates, and the right panel shows relative errors of the standard linear regression average glucose estimates as a function of errors of the patient-specific model average glucose estimates. The data points shown in both the left panel and the right panel include data from four patient sets.

FIG. 6 compares the AG estimation errors of both methods for each patient. The left panel of FIG. 6 shows the standard regression estimate error on the x-axis versus the excess error for the standard regression estimates compared to the patient-specific model. The patient-specific model has a smaller range of errors overall. In the minority of cases where the standard regression error is smaller, the range of patient-specific model errors is smaller than that for the cases where the patient-specific model is more accurate than the standard regression error. The majority of points have positive y-values (are above the horizontal black line) demonstrating that the patient-specific model is more accurate and that the excess prediction error for the standard regression method can be almost 50 mg/dL. The points with negative y-values are slightly more accurately estimated by the standard regression method, but the patient-specific model estimates are less than 10 mg/dL in most cases and greater than 20 mg/dL only once. The right panel of FIG. 6 shows the same y-values as a function of the patient specific-model estimation errors. The x-axis range of the right panel (0-25 mg/dL) is half that of the left panel (0-50 mg/dL) because the patient-specific model errors are smaller overall.

Figure 7:
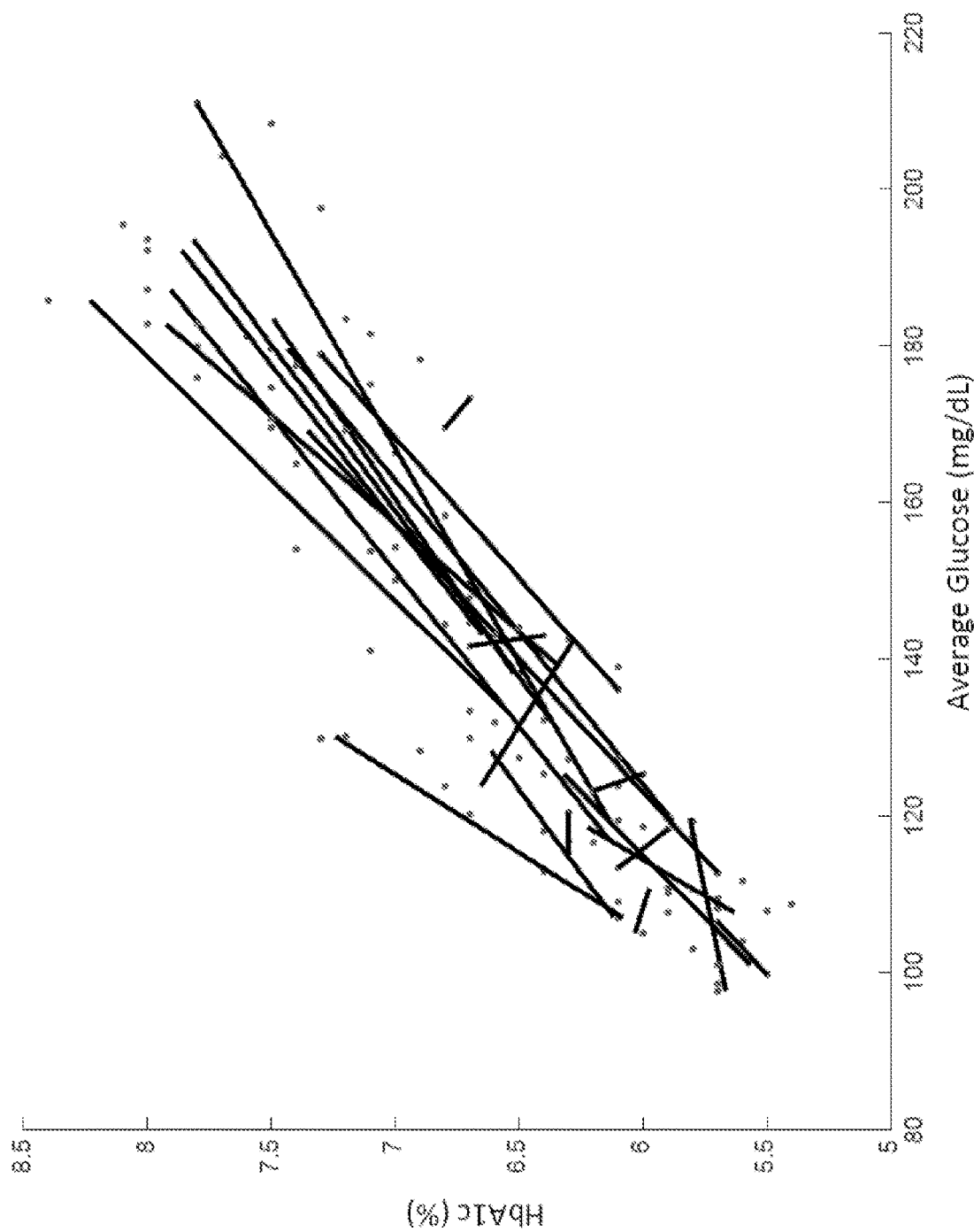
FIG. 7 illustrates a plot of average glucose and glycated hemoglobin values for several patients overlaid with best fit graphs relating average glucose and glycated hemoglobin for each patient.

In some cases, there is uncertainty in each patient-specific slope. FIG. 7 plots AG on the x-axis and HbA1c on the y-axis for patients in Patient Set #2, along with linear fits for each intra-patient set of measurements. Each black line represents a best-fit linear regression for a single patient. The uncertainty for each regression fit is significant given the small number of measurements for each patient. The few negative slopes represent measurement error and/or short-term changes in $M_{RBC}$. Among patients with more than 3 pairs of measurements, the mean slope is 0.023+/−0.019 (%-dL/mg). The patient-specific slopes show significant variation with a mean of 0.023 (%-dL/mg) and a confidence interval spanning 0.019 (%-dL/mg).

The difference in AG between a non-diabetic (HbA1c<6.5%) and a diabetic with sub-optimal disease control (HbA1c>7.0%) can be ~15 mg/dL (9). Thus, errors of 15 mg/dL or less in estimated AG could mislead clinicians and patients and compromise patient care and optimal management of long-term risk of complications. Across the 4 sets of patients, the standard regression method generated AG estimation errors greater than 15 mg/dL for about 1 patient in 3 (31.4%), while the patient-specific model produced errors this large for only 1 patient in 10 (9.6%). An error in estimated AG of 28.7 mg/dL is equivalent to an error of ~1.0% in HbA1c. The standard regression method generated AG estimation errors at least this large for 1 patient in 13, and the patient-specific method for only 1 patient in 220.

Example 2: Personalizing the Model for Increased Accuracy of Prospectively-Estimated AG An accurate estimate of AG can improve diagnosis and management of diabetes. In Example 1, factors determining AG-independent variation in HbA1c were quantified by developing a patient-specific mechanistic mathematical model describing how HbA1c depends on the chemical kinetics of hemoglobin glycation in a population of RBCs at dynamic equilibrium. As described with respect to Example 2, a patient-specific correction factor ($\widetilde{M_{RBC}}$) was derived to improve the accuracy of AG estimation from HbA1c. The prospective utility of $\widetilde{M_{RBC}}$ to improve accuracy can be consistent in individuals over time. The improvement in AG calculation afforded by the patient-specific model can improve medical care and provide for a patient-specific approach to determining AG from HbA1c.

Using the patient-specific model, one pair of CGM-measured AG and an HbA1c measurement was used to determine the M patient's $\widetilde{M_{RBC}}$. This pair of measurements represents baselined data for future estimates of AG and HbA1c amount. $\widetilde{M_{RBC}}$ was used to refine the future AG calculated based on HbA1c. In the examples described herein, the mechanistic mathematical model described with respect to Example 1 was combined with CGM measurements to personalize the model for each patient. The patient-specific model was used in combination with one set of CGM and HbA1c data to derive the patient's $\widetilde{M_{RBC}}$ and to predict an estimated AG from future HbA1c. The accuracy of estimates of AG made using the patient-specific model was compared with the accuracy of estimates made using a standard regression method in which glucose-independent variation is not considered.

Because $CV(M_{RBC}) \approx CV(\hat{\theta})$, a patient's $M_{RBC}$ can be estimated using published estimates of $[1-HbA1c(0)]$ and $k_g$:

$$\widetilde{M_{RBC}} = \frac{\hat{\theta}}{[1-HbA1c(0)] \cdot k_g}.$$

The symbol $\widetilde{M_{RBC}}$ is used to represent an estimate of the patient's true $M_{RBC}$. $M_{RBC}$ can be tightly regulated within individuals. It was hypothesized that a patient-specific $\widetilde{M_{RBC}}$ can be derived at one point in time and can be used prospectively through Equation (4) to improve the accuracy of future AG estimates made from future HbA1c:

$$AG = \frac{HbA1c - HbA1c(0)}{[1-HbA1c(0)] \cdot k_g \cdot \widetilde{M_{RBC}}}.$$

Figure 4:
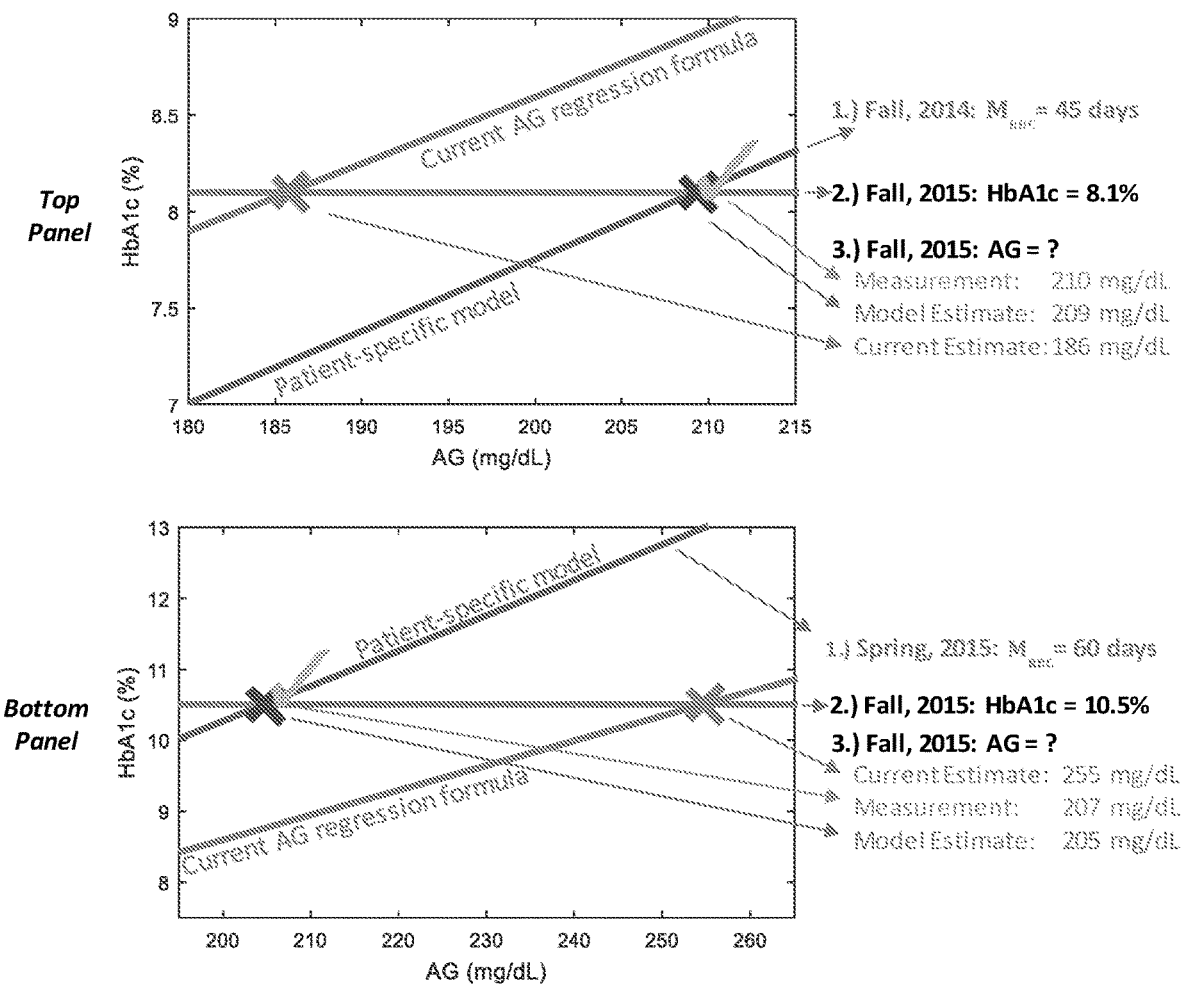
FIG. 4 includes top and bottom panels showing values of average glucose estimated using a standard linear regression and values of average glucose using patient-specific models for two different patients.

FIG. 4 depicts two examples. While a linearized model and analysis are presented in this example, similar results can be obtained with an exact numerical solution, as described with respect to Example 4 herein. AG estimates for 16 HbA1c measurements from 9 distinct adult patients at Massachusetts General Hospital were evaluated.

The top panel of FIG. 4 shows that one patient's modeled $M_{RBC}$ was 45 days in the fall of 2014. The blue line (#1) shows the $M_{RBC}$-adjusted AG-HbA1c relationship personalized for this patient, in contrast to the red line showing the standard AG-HbA1c formula. One year after the $M_{RBC}$ estimation, the patient visited the clinic and had an HbA1c of 8.1% (gray horizontal line, #2). The linear standard method predicted an AG of 186 mg/dL (red "X"). The model predicted 209 mg/dL (blue "X"). This patient had CGM data available providing a direct and independent measurement of AG equal to 210 mg/dL (green checkmark). This patient's personalized AG-HbA1c model reduced the error in AG estimation from 24 mg/dL to 1 mg/dL.

The bottom panel of FIG. 4 shows that a second patient had a model-estimated $M_{RBC}$ of 60 days in the spring of 2015, yielding a personalized AG-HbA1c relationship corresponding to the blue line (#1, bottom panel) in contrast to the red line showing the standard formula. About 6 months later in the fall of 2015, the patient returned to the clinic and had an HbA1c of 10.5% (gray horizontal line, #2). The standard method predicted an AG of 255 mg/dL (red "X"). The model predicted 205 mg/dL (blue "X"). This patient had CGM data available providing a direct and independent measurement of AG equal to 207 mg/dL (green checkmark). This patient's personalized AG-HbA1c model reduced the error in AG estimation from 48 mg/dL to 2 mg/dL.

These two examples highlight the fact that, with the standard method, a patient with lower AG (as shown in the top panel of FIG. 4) may actually have a significantly higher HbA1c than a patient with a higher AG (as shown in bottom panel of FIG. 4). Such a discrepancy can compromise disease diagnosis and management.

Example 3: Real-Time Estimates of HbA1c for Patients with CGM

A method to estimate HbA1c from CGM in real-time can provide useful feedback for patients trying to optimize glucose management between clinic visits. Patients may be accustomed to thinking about the quality of their glucose control in terms of HbA1c. Previous studies have developed sophisticated methods to estimate HbA1c by combining prior HbA1c levels with multipoint profiles of self-monitored glucose (26). These methods can achieve correlation between estimated and measured HbA1c as high as 0.76, with estimates of HbA1c deviating from measured HbA1c by an average of as little as 0.5%. For example, if the measured HbA1c was 7.0%, this method can estimate an HbA1c between 6.5% and 7.5%. The patient-specific model presented here may have two advantages over other approaches in that (i) it controls for patient-specific variation in non-glycemic factors influencing HbA1c, and (ii) it takes advantage of glucose characterization provided by CGM. The patient-specific method can estimate HbA1c with higher accuracy.

HbA1c for 200 patients was estimated in the study populations described with respect to Example 1. A correlation of 0.90 and an average deviation from measured HbA1c of 0.3% were determined. In this regard, if the measured HbA1c was 7.0%, the patient-specific method can estimate an HbA1c between 6.7% and 7.3%. Given that analytic variation in HbA1c assays would be expected to generate an uncertainty range of at least 6.9%-7.1% (27), the patient-specific model can thus make a significant advance toward optimal estimation of HbA1c amount.

Example 4: Numerical Solution

The physiologic model for glycation can be solved numerically without making a linear approximation. Modeling and statistical analyses were performed in MATLAB (MathWorks, Inc.). The differential equation model can include a time-varying glucose concentration (G(t)):

$$\frac{d}{dt}gHb(t) = k_g \cdot G(t) \cdot (tHb - gHb(t)) \quad (8)$$

This equation can be integrated numerically to provide the HbA1c amount in an RBC of age t:

$$HbA1c(t) = HbA1c(0) + \frac{k_g}{tHb} \cdot \int_0^t G(\tau) \cdot (tHb - gHb(\tau))d\tau \quad (9)$$

The clinical HbA1c measurement is the average over a uniform distribution of RBC ages ranging between 0 and $2 \cdot M_{RBC}$:

$$HbA1c = \quad (10)$$

$$\frac{1}{2 \cdot M_{RBC}} \int_0^{2 \cdot M_{RBC}} \left[ HbA1c(0) + \frac{k_g}{tHb} \cdot \int_0^t G(\tau) \cdot (tHb - gHb(\tau))d\tau \right] dt$$

Given sufficient CGM data to define $G(\tau)$ and a concurrent HbA1c measurement, the above equation can be solved numerically for $M_{RBC}$ to provide a patient-specific $\widetilde{M_{RBC}}$. For the model-based prediction of AG from HbA1c, the patient's $\widetilde{M_{RBC}}$ is used, and the following equation is solved numerically for AG:

$$HbA1c = \frac{1}{2 \cdot \widetilde{M_{RBC}}} \int_0^{2 \cdot \widetilde{M_{RBC}}} \left[ HbA1c(0) + AG \cdot \frac{k_g}{tHb} \cdot \int_0^t (tHb - gHb(\tau))d\tau \right] dt \quad (11)$$

Example 5: Further Example of Deriving AG-HbA1c Linear Relationship

Example 5A-5F describe an example of deriving the linear relationship between AG and HbA1c from a physiological model of glycation and validating this derivation.

Example 5A: Derivation of the AG-HbA1c Linear Regression from the Physiological Model of Glycation The derivation of the regression equation (4) is based on prior studies of hemoglobin as summarized below in "Synopsis of prior models of hemoglobin glycation." The assumptions used in the physiologic model development are detailed below in Example 5F. The derivation starts from the linearized model of chemical kinetics for a single RBC (Equation (3)):

$$HbA1c = HbA1c(0) + [1 - HbA1c(0)] \cdot k_g \cdot t \cdot AG \quad (12)$$

Two steps of the conditional expectation (i.e., averaging) operation are performed. The first is the averaging over the age of the RBCs in a single blood sample, because the RBCs in a single blood sample have heterogeneous age. The second averaging is over the model parameters which may vary from one person to the next. In this case, the parameters are specifically defined to be glycation rate, ($k_g$), reticulocyte HbA1c $$\left(\frac{gHb(0)}{tHb}\right),$$

and the RBC age ($M_{RBC}$). The final step is to apply the conditional expectation operator (conditioning on AG) to the result of the first conditional expectation and derive the known linear regression relationship between AG and the HbA1c amount, equivalent to equation (4):

$$\mathbb{E}\{HbA1c|AG\} = \alpha \cdot AG + \beta \quad (13)$$

The slope of the regression line is represented by $\alpha$ and the y-intercept by $\beta$, where $\mathbb{E}\{\cdot\}$ represents the expectation or averaging operation, and $\mathbb{E}\{\cdot|W\}$ represents the conditional expectation or averaging with respect to a restricting condition W. For example, $\mathbb{E}\{HbA1c|AG\}$ in general will be function of AG, (in this case the function is: $\alpha \cdot AG + \beta$), and as values of HbA1c are averaged while restricting to AG=ag, a different average HbA1c is obtained for each AG value or range. The AG is, for example, restricted to be within a range e.g., ±5 (mg/dL).

FIG. 1 shows a regression line, equivalent to performing the above calculation of $\mathbb{E}\{HbA1c|AG\}$ on the ADAG dataset. Analyzing the biochemical process as the average of Equation (4) shows that the regression line's intercept ($\beta$) is controlled by $$\left(\frac{gHb(0)}{tHb}\right)$$

when the cells are introduced to the circulation:

$$\beta = \mathbb{E}\left\{\frac{gHb(0)}{tHb}\right\} \quad (14)$$

The regression's slope ($\alpha$) is controlled by the average glycation rate, $\mathbb{E}\{k_g\}$, and $M_{RBC} = \mathbb{E}\{t|\tau\}$, where $\tau$ is a set of parameters defining the patient's RBC age distribution:

$$\alpha = \mathbb{E}_p\left\{\mathbb{E}\{k_g\} \cdot \mathbb{E}\{t|\tau\} \cdot \left(1 - \frac{gHb(0)}{tHb}\right)\right\} \quad (15)$$

The reticulocyte HbA1c can play a more minor role because it is relatively small (~0.003) and even doubling this amount would alter its contribution to a through the term $$\left(1 - \frac{gHb(0)}{tHb}\right)$$

from 0.997 to 0.994, and difference of 0.3%.

Figure 8A:
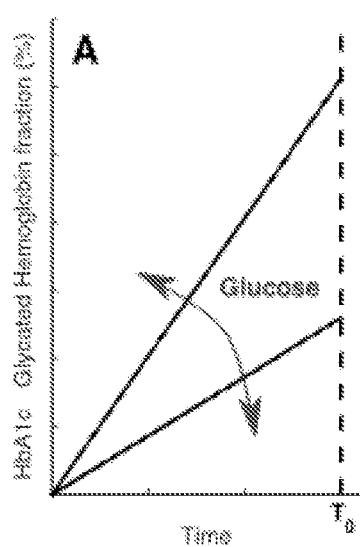
FIG. 8A shows a graph of glycated hemoglobin fraction over time.
Figure 8B:
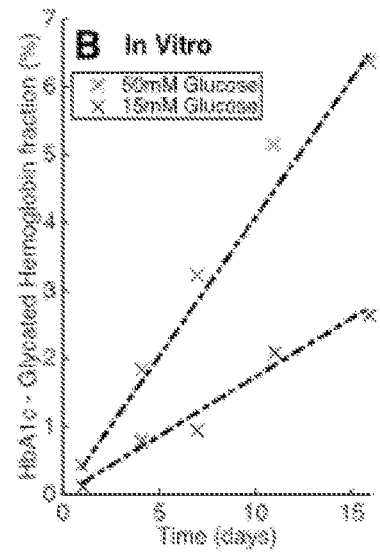
FIG. 8B shows a plot of in vitro measurements of glycated hemoglobin fraction over time overlaid on the graph of FIG. 8A. The upper line and data points refer to measurements of glycated hemoglobin fraction when hemoglobin is incubated with a glucose concentration of 50 mM. The bottom line and data points refer to measurements of glycated hemoglobin fraction when hemoglobin is incubated with a glucose concentration of 15 mM.
Figure 8C:
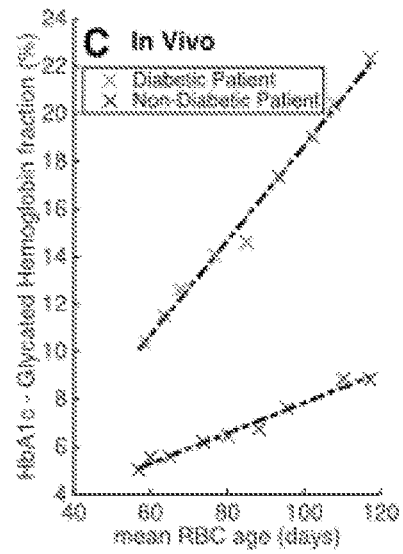
FIG. 8C shows a plot of in vivo measurements of glycated hemoglobin fraction over time overlaid on the graph of FIG. 8A. The upper line and data points refer to measurements of glycated hemoglobin fraction in a diabetic patient. The lower line and data points refer to measurements of glycated hemoglobin fraction in a non-diabetic patient.

An equation in the form of Equation (15): y=m·b·x generates structurally unidentifiable parameters m and b when x and y are the only observations. m and b cannot be uniquely estimated. FIGS. 8A-8C illustrate that both AG and $M_{RBC}$ control the slope. The chemical reaction equation encodes the accumulation of glycated hemoglobin (HbA1c).

FIG. 8A shows that the two main factors controlling the rate of accumulation of HbA1c (slope) are: (1) the time ($T_0$) over which the reaction product can accumulate, and (2) the glucose abundance or concentration.

FIG. 8B illustrates that in vitro incubation of Hb with two glucose concentrations for 16 days validated the linear relationship ($r^2$ is 0.95 (15 mM) and 0.97 (50 mM)). The incubation also validated the contribution of both incubation time and glucose concentration to the level of HbA1c. The experimental data for FIG. 8B were from Reference (2).

FIG. 8C illustrates that in vivo repeated sampling of biotin-labeled RBCs from diabetic and non-diabetic human subjects also validated the linear relationship ($r^2$=0.99, 0.96 respectively). This example also validated the fact that in vivo HbA1c levels were controlled by the same two factors: (1) accumulation time (samples are taken farther and farther from the time of RBC labeling), that is, mean RBC age, and (2) glucose concentration. The patients with diabetes had higher AG. Experimental data for FIG. 6C were from Reference (3).

In order to overcome the issue that m and b cannot be unique estimated, a stable age distribution and the independence of $k_g$ from $M_{RBC}$ were assumed. These assumptions were combined with the notation $M_{RBC} = \mathbb{E}_t\{t|\tau\}$ to simplify Equation (15) and the expression for the regression slope:

$$\alpha = \mathbb{E}\{k_g\} \cdot (1-\beta) \cdot \mathbb{E}\{M_{RBC}\} \quad (16)$$

In order to perform the two steps of conditional expectation, p is defined as the collection of model parameters along with a set of parameters ($\tau$) which defines the patient's RBC age distribution whose mean is $M_{RBC}$:

$$p = \left\{k_g, \frac{gHb(0)}{tHb}, \tau\right\}.$$

The first conditional expectation is applied in the context of an individual patient and reflects the fact that each clinical measurement of an amount of HbA1c is the average of the HbA1c amount in millions of RBCs from that patient, and those RBCs have different ages. The intra-patient conditional expectation step ($\mathbb{E}_t\{\cdot|AG,p\}$) averages over t, the ages of individual RBCs, and leads to following equation for a given AG and p:

$$\mathbb{E}_t\{HbA1c | AG, p\} = \quad (17)$$

$$AG \cdot \mathbb{E}_t\left\{k_g \cdot t \cdot \left(1 - \frac{gHb(0)}{tHb}\right) \bigg| p\right\} + \mathbb{E}_t\left\{\frac{gHb(0)}{tHb} \bigg| p\right\}$$

Hence $M_{RBC}$ represents the mean RBC age for a given individual at the time of the HbA1c measurement but can vary from one person to the next. The RBC population is assumed to be at steady state and to have a time-invariant age distribution. This assumption is insensitive to the underlying RBC elimination mechanism, as long as the RBC population is in homeostasis. Also assuming independence between the components of p allows us to simplify Equation (17):

$$\mathbb{E}_t\{HbA1c \mid AG, p\} = AG \cdot k_g \cdot \left(1 - \frac{gHb(0)}{tHb}\right) \cdot M_{RBC} + \frac{gHb(0)}{tHb} \quad (18)$$

This last step completes the first conditional expectation calculation. The model in this form is the theoretical equivalent to a single patient's HbA1c measurement, and it implies that, for a given individual, a linear relationship is expected to hold with variation in the slope and intercept, as observed in Reference (43). To reproduce the observed regression relationship (FIG. 1), AG is controlled and the expression is averaged over the variability in the personal parameters (p), i.e. the second conditional expectation step:

$$\mathbb{E}_p\{HbA1c \mid AG\} = \quad (19)$$
$$AG \cdot \mathbb{E}_p\left\{k_g \cdot \left(1 - \frac{gHb(0)}{tHb}\right) \cdot \mathbb{E}_t\{t \mid M_{RBC}\}\right\} + \mathbb{E}_p\left\{\frac{gHb(0)}{tHb}\right\}$$

This equation is the basis for the derivation of Equations (14) and (15).

The (AG, HbA1c) data from multiple studies were fit using a linear regression model. For the ADAG study, $r^2=0.84$, and the regression parameters are estimated as $\alpha=3.2\cdot10^{-4}$ with confidence interval $(3.1\cdot10^{-4}, 3.3\cdot10^{-4})$. and $\beta=0.0032$ (0.0014, 0.0051). $\beta$ is multiplied by 100 to be converted to a percentage. $\beta$ estimated in the ADAG thus is equivalent to an HbA1c of 0.32%.

The regression for the ADAG in FIG. 1 differs from that published, because the bias in the HbA1c clinical measurements is corrected using the NGSP standards (41). To obtain the above estimated regression parameters, the values reported in FIG. 1 have been transformed using: $z(x)=(x-2.153)/0.915$. In one study, survival of labeled RBCs was measured to yield $M_{RBC}$. The reported quantity is different (and has different units) from the $k_g$ reported in Example 5A. First, it is about two orders of magnitude higher than values reported for $k_g$, and second, it has units of $$\frac{1}{\text{time}},$$

rather than $$\frac{\left(\frac{mg}{dL}\right)}{\text{time}}.$$

The difference ensues from the derivation of these values as the slopes in the relationship between HbA1c and $M_{RBC}$. Thus, in terms of the model discussed here, these reported values correspond to $k_g \cdot AG$, explaining the additional factor of $\approx 100$. AG can be expected to change across patients, in particular, between diabetic and non-diabetic subjects.

The ADAG estimate of the regression intercept in the patient-specific model is $$\hat{\mathbb{E}}\left\{\frac{gHb(0)}{tHb}\right\} = \hat{\beta} = 0.0032.$$

$\mathbb{E}\{M_{RBC}\}$ can be defined to be 53 days (41). Using the above estimate for $\alpha$, the average glycation rate can be estimated:

$$\hat{\mathbb{E}}\{k_g\} = \frac{\hat{\alpha}}{M_{RBC}(1-\hat{\beta})} = \frac{3.2\cdot10^{-4}}{53\cdot0.997} = 6.07\cdot10^{-6} \; dl/mg/day \quad (20)$$

This estimate is consistent with other estimates of glycation rates (14): $(6.07\cdot10^{-6}\text{–}10.30\cdot10^{-6})$. Some reports of estimated glycation rate constants ($k_g$) can neglect red cell aging or assume a fixed $M_{RBC}$ (of 60 days) for all RBCs and all subjects (12, 44, 45).

The modeling and analysis in Example 5A is based on the use of NGSP HbA1c measurements (41). These methods can produce an average positive measurement bias of about 2%, which is more significant than the level of initial glycation fraction in reticulocytes (~0.5%). In some examples to implement the proposed correction in a clinical setting, each patient's actual bias (and stability) can be estimated with respect to the specific lab instrument that is used to monitor the patient's HbA1c values.

Example 5B: RBC Maturation in the Bone Marrow

The patient-specific model can be valid in the bone marrow in which the initial value $$\frac{gHb(0)}{tHb} = 0.$$

For the model to hold, the glycation process needs to start after all hemoglobin has been synthesized because the hemoglobin concentration is assumed to not be changing with time due to hemoglobin synthesis or changes in the RBC volume. This assumption makes the model's application to the glycation of hemoglobin in RBCs that are in bone marrow a rough estimate. Using the estimated $\beta$, the time the RBCs spend in the bone marrow can be estimated:

$$\left(\mathbb{E}\left\{\frac{gHb(t)}{tHb}\,\bigg|\,AG\right\}\right) = k_g \cdot AG \cdot t \Rightarrow \quad (21)$$
$$0.0032 = 6.07\cdot10^{-6} \cdot 100 \cdot \mathbb{E}\{t\} \Rightarrow$$
$$\mathbb{E}\{t\} = \frac{0.0032}{6.07\cdot10^{-6} \cdot 100} = 5.3 \; days$$

This estimate is consistent with results of other examples that have measured the amount of time that RBCs spend in the bone marrow (3). The direct average HbA1c in transferrin receptor-positive reticulocytes was found to be 0.0074 (4). This value is consistent with the value obtained from the regression intercept. The fact that the value is higher is expected as the NGSP-approved HbA1c measurement methods have a general positive bias with respect to a gold standard (as all other clinical methods), but the size of the bias was not quantified in this range of values, and HbA1c levels below 2% will become negative when using the recommended correction (41), which is intended for HbA1c bias in general RBC populations, not reticulocytes.

Example 5C: Theoretical Modeling Assumptions

The assumptions have been noted previously in the text and are enumerated here for reference with additional clarifications.

A1. Hemoglobin glycation is irreversible (as described by Equation (2)).
A2. An RBC has a time invariant concentration of hemoglobin. This assumption contradicts observations of increased concentration (47). However, the concentration of a single RBC increases slightly with age, and the changes in hemoglobin concentration described at the level of the population are relatively small (~10%).
A3. The first order approximation for the glycation model is valid. This assumption is based on the validity of $e^x \approx 1+x$.
A4. The RBC age distribution has first and second moments.
A5. The glycation rate $k_g$ is constant across individuals.
A6. The personal parameters $$\left(k_g, \frac{gHb(0)}{tHb}, M_{RBC}\right)$$

are statistically independent.
A7. The RBC age distribution is at steady-state (time invariant).
A8. The average initial glycation $$\left(\mathbb{E}\left\{\frac{gHb(0)}{tHb}\right\}\right)$$

is constant in the population.

Example 6: Estimation of RBC Flux

Accurate estimation of RBC flux in the clinical context can be challenging. If N represents the number of RBCs in circulation, then $$\frac{dN}{dt}(t)$$

is the instantaneous net RBC flux and is determined by the instantaneous RBC birth rate (b(t)) and the instantaneous RBC clearance rate (c(t)):

$$\frac{dN}{dt}(t) = b(t) - c(t).$$

Accurate estimation of $$\frac{dN}{dt}(t)$$

can thereby benefit from accurate measurements of both b(t) and c(t). The reticulocyte count provides an estimate of b(t) averaged over a couple of days. This estimate can have significant variability even on repeat measurements from the same blood sample (24, 48). For the purpose of modeling average levels of glycated hemoglobin, the RBC flux averaged over at least a couple of weeks can be estimated. In patients without severe disease, N is assumed to not vary significantly: $N(t) \approx N_c$. Under these assumptions, mean RBC age ($M_{RBC}$) and RBC lifespan provide estimates of the several-week average of RBC flux in units of percent of the circulating RBC population turned over per unit time. In other words, for $\tau^* > \sim 2$ weeks:

$$\int_0^{\tau^*} \frac{dN}{dt}(\tau)d\tau = \int_0^{\tau^*} b(\tau) - c(\tau)d\tau \approx 0$$

The flux in and the flux out are balanced and can be estimated from the RBC lifespan or $M_{RBC}$:

$$\frac{1}{N_c \cdot \tau^*} \int_0^{\tau^*} b(\tau)d\tau \approx \frac{1}{N_c \cdot \tau^*} \int_0^{\tau^*} c(\tau)d\tau \approx \frac{1}{2 * M_{RBC}} \approx \frac{1}{RBC\ lifespan}$$

In this regard, in this example, methods for measuring $M_{RBC}$ or RBC lifespan relying on labeling and repeated resampling of blood can provide adequate estimates of average RBC flux (16). Mathematical model-based methods to estimate RBC flux are also available and are likely less accurate but do not require invasive methods like labeling and repeated resampling (24, 40).

REFERENCES

The following publications are incorporated by reference in their entirety and referenced throughout the application in parentheses:
1. D. M. Nathan et al., Translating the A1C assay into estimated average glucose values. *Diabetes Care* 31, 1473 (2008).
2. P. J. Higgins, H. F. Bunn, Kinetic-Analysis of the Non-Enzymatic Glycosylation of Hemoglobin. *Journal of Biological Chemistry* 256, 5204 (1981).
3. R. M. Cohen et al., Red cell life span heterogeneity in hematologically normal people is sufficient to alter HbA1c. *Blood* 112, 4284 (November, 2008).
4. P. K. Khera et al., Use of an oral stable isotope label to confirm variation in red blood cell mean age that influences HbA1c interpretation. *Am. J. Hematol.* 90, 50 (2015).
5. International Diabetes Foundation, in *IDF Diabetes Atlas* (http://www.idf.org/diabetesatlas). (2015).
6. DCCT Research Group, The effect of intensive treatment of diabetes on the development and progression of long-term complications in insulin-dependent diabetes mellitus. *N Engl J Med* 329, 977 (1993).
7. U. P. D. S. G. (UKPDS), others, Intensive blood-glucose control with sulphonylureas or insulin compared with conventional treatment and risk of complications in patients with type 2 diabetes (UKPDS 33). *The Lancet* 352, 837 (1998).
8. D. B. Sacks, Hemoglobin A1 c in diabetes: panacea or pointless? *Diabetes* 62, 41 (2013).
9. American Diabetes Association, Standards of medical care in diabetes—2010. *Diabetes care* 33, S11 (2010).
10. P. K. Crane et al., Glucose levels and risk of dementia. *New England Journal of Medicine* 369, 540 (2013).

11. H. F. Bunn, D. N. Haney, S. Kamin, K. Gabbay, P. Gallop, The biosynthesis of human hemoglobin A1 c. Slow glycosylation of hemoglobin in vivo. *Journal of Clinical Investigation* 57, 1652 (1976).
12. K. W. Beach, A theoretical model to predict the behavior of glycosylated hemoglobin levels. *Journal of theoretical biology* 81, 547 (1979).
13. P. Ladyzynski et al., Validation of hemoglobin glycation models using glycemia monitoring in vivo and culturing of erythrocytes in vitro. *Annals of biomedical engineering* 36, 1188 (2008).
14. R. Lledó-García, N. A. Mazer, M. O. Karlsson, A semi-mechanistic model of the relationship between average glucose and HbA1c in healthy and diabetic subjects. *Journal of pharmacokinetics and pharmacodynamics* 40, 129 (2013).
15. S. M. Osterman-Golkar, H. W. Vesper, Assessment of the relationship between glucose and A1 c using kinetic modeling. *Journal of Diabetes and its Complications* 20, 285 (2006).
16. R. S. Franco, The measurement and importance of red cell survival. *Am. J. Hematol.* 84, 109 (February, 2009).
17. C. Rohlfing et al., Biological variation of glycohemoglobin. *Clinical Chemistry* 48, 1116 (July, 2002).
18. B. J. Gould, S. J. Davie, J. S. Yudkin, Investigation of the mechanism underlying the variability of glycated haemoglobin in non-diabetic subjects not related to glycaemia. *Clin. Chim. Acta* 260, 49 (April, 1997).
19. R. M. Cohen, Y. R. Holmes, T. C. Chenier, C. H. Joiner, Discordance between HbA(1c) and fructosamine—Evidence for a glycosylation gap and its relation to diabetic nephropathy. *Diabetes Care* 26, 163 (January, 2003).
20. J. S. Yudkin et al., Unexplained Variability of Glycated Hemoglobin in Nondiabetic Subjects Not Related to Glycemia. *Diabetologia* 33, 208 (April, 1990).
21. P. Ladyzynski et al., Hemoglobin glycation rate constant in non-diabetic individuals. *Annals of biomedical engineering* 39, 2721 (2011).
22. Y. Tahara, K. Shima, Kinetics of HbA(1c), glycated albumin, and fructosamine and analysis of their weight-functions against preceding plasma-glucose level. *Diabetes Care* 18, 440 (April, 1995).
23. J. M. Higgins, L. Mahadevan, Physiological and pathological population dynamics of circulating human red blood cells. *Proceedings of the National Academy of Sciences* 107, 20587 (2010).
24. H. H. Patel, H. R. Patel, J. M. Higgins, Modulation of red blood cell population dynamics is a fundamental homeostatic response to disease. *American journal of hematology* 90, 422 (2015).
25. M. S. Golub, C. E. Hogrefe, R. Malka, J. M. Higgins, Developmental plasticity of red blood cell homeostasis. *Am. J. Hematol.* 89, 459 (May, 2014).
26. B. P. Kovatchev, F. Flacke, J. Sieber, M. D. Breton, Accuracy and Robustness of Dynamical Tracking of Average Glycemia (A1 c) to Provide Real-Time Estimation of Hemoglobin A1 c Using Routine Self-Monitored Blood Glucose Data. *Diabetes Technol. Ther.* 16, 303 (May, 2014).
27. E. Lenters-Westra, R. J. Slingerland, Six of Eight Hemoglobin A(1c) Point-of-Care Instruments Do Not Meet the General Accepted Analytical Performance Criteria. *Clinical chemistry* 56, 44 (January, 2010).
28. D. R. Matthews et al., Homeostasis model assessment: insulin resistance and beta-cell function from fasting plasma glucose and insulin concentrations in man. *Diabetologia* 28, 412 (July, 1985).
29. F. H. El-Khatib, S. J. Russell, D. M. Nathan, R. G. Sutherlin, E. R. Damiano, A Bihormonal Closed-Loop Artificial Pancreas for Type 1 Diabetes. *Science Translational Medicine* 2, (April, 2010).
30. Y. Q. Wang, E. Dassau, F. J. Doyle, Closed-Loop Control of Artificial Pancreatic beta-Cell in Type 1 Diabetes Mellitus Using Model Predictive Iterative Learning Control. *IEEE Trans. Biomed. Eng.* 57, 211 (February, 2010).
31. R. N. Bergman, L. S. Phillips, C. Cobelli, Physiologic Evaluation Of Factors Controlling Glucose-Tolerance in Man—Measurement of Insulin Sensitivity and Beta-Cell Glucose Sensitivity from the Response to Intravenous Glucose. *Journal of Clinical Investigation* 68, 1456 (1981).
32. R. N. Bergman, Toward Physiological Understanding of Glucose-Tolerance—Minimal-Model Approach. *Diabetes* 38, 1512 (December, 1989).
33. R. Ali, J. Hussain, M. H. Siddiqi, M. Hussain, S. Lee, H2RM: A Hybrid Rough Set Reasoning Model for Prediction and Management of Diabetes Mellitus. *Sensors* 15, 15921 (July, 2015).
34. E. I. Georga, V. C. Protopappas, D. Polyzos, D. I. Fotiadis, Evaluation of short-term predictors of glucose concentration in type 1 diabetes combining feature ranking with regression models. *Medical & Biological Engineering & Computing* 53, 1305 (December, 2015).
35. C. Zecchin, A. Facchinetti, G. Sparacino, C. Cobelli, in *Artificial Neural Networks, 2nd Edition*, H. Cartwright, Ed. (2015), vol. 1260, pp. 245-259.
36. C. L. Huang et al., Using Hemoglobin A1C as a Predicting Model for Time Interval from Pre-Diabetes Progressing to Diabetes. *Plos One* 9, (August, 2014).
37. J. E. Given, B. P. Bunting, V. E. Coates, M. J. O'Kane, Measurement error in estimated average glucose: a novel approach. *Clinical Chemistry and Laboratory Medicine* 52, E147 (July, 2014).
38. A. Barua, J. Acharya, S. Ghaskadbi, P. Goel, The relationship between fasting plasma glucose and HbA(1c) during intensive periods of glucose control in antidiabetic therapy. *J. Theor. Biol.* 363, 158 (December, 2014).
39. E. R. Damiano et al., A comparative effectiveness analysis of three continuous glucose monitors: the Navigator, G4 Platinum, and Enlite. *Journal of diabetes science and technology* 8, 699 (2014-July, 2014).
40. J. M. Higgins, L. Mahadevan, Physiological and pathological population dynamics of circulating human red blood cells. *Proc. Natl. Acad. Sci. U.S.A.* 107, 20587 (November, 2010).
41. W. Hoelzel et al., IFCC reference system for measurement of hemoglobin A1 c in human blood and the national standardization schemes in the United States, Japan, and Sweden: a method-comparison study. *Clinical chemistry* 50, 166 (2004).
42. R. M. Cohen, R. S. Franco, C. H. Joiner, Is poor glycemic control associated with reduced red blood cell lifespan? *Diabetes care* 27, 1013 (2004).
43. J. M. Hempe, R. Gomez, R. J. McCarter, S. A. Chalew, High and low hemoglobin glycation phenotypes in type 1 diabetes: a challenge for interpretation of glycemic control. *Journal of diabetes and its complications* 16, 313 (2002).
44. P. J. Higgins, H. F. Bunn, Kinetic analysis of the nonenzymatic glycosylation of hemoglobin. *Journal of Biological Chemistry* 256, 5204 (1981).

45. H. B. Mortensen, A. Vølund, C. Christophersen, Glucosylation of human haemoglobin a. dynamic variation in HbA1c described by a biokinetic model. *Clinica chimica acta* 136, 75 (1984).
46. H. Jansen et al., Determinants of HbA1c in nondiabetic Dutch adults: genetic loci and clinical and lifestyle parameters, and their interactions in the lifelines cohort study. *Journal of internal medicine* 273, 283 (2013).
47. R. Malka, F. F. Delgado, S. R. Manalis, J. M. Higgins, In vivo volume and hemoglobin dynamics of human red blood cells. *PLoS Comput. Biol.* 10, (2014).
48. E. Piva, C. Brugnara, L. Chiandetti, M. Plebani, Automated reticulocyte counting: state of the art and clinical applications in the evaluation of erythropoiesis. *Clinical Chemistry and Laboratory Medicine* 48, 1369 (October, 2010).

What is claimed is:

1. A method comprising:
    estimating a value of a parameter indicative of an age or lifespan of a population of red blood cells of a subject;
    estimating a value of average glucose (AG) of the subject based on (i) the value of the parameter and (ii) a value indicative of an amount of glycated hemoglobin (HbA1c) of the subject; and
    administering an amount of insulin or insulin analog to the subject to treat a hyperglycemia condition of the subject, the amount of the insulin or insulin analogue being a function of the estimated value of AG.

2. The method of claim 1, wherein the value of the parameter is indicative of at least one of an average red blood cell age (MRBC), a half-life of a red blood cell population, or an average red blood cell lifespan.

3. The method of claim 1, wherein the value indicative of the amount of HbA1c is a second value indicative of the amount of HbA1c, and the value of the parameter is estimated based on a first value indicative of the amount of HbA1c and a value indicative of blood glucose concentration of the subject.

4. The method of claim 3, wherein the first value indicative of the amount of HbA1c is measured at a first time after a time period in which the value indicative of blood glucose concentration of the subject is measured.

5. The method of claim 4, wherein the first time is earlier than a second time at which the second value indicative of the amount of HbA1c is measured.

6. The method of claim 1, wherein estimating the value of the parameter comprises estimating the value of the parameter based on a plurality of measurements collected by a continuous glucose monitoring (CGM) device.

7. The method of claim 6, wherein the measurements are collected over a period of time of at least 7 days.

8. The method of claim 1, wherein the parameter is estimated based on a weighted average of multiple values indicative of blood glucose concentration of the subject.

9. The method of claim 8, wherein:
    the value indicative of the amount of HbA1c is a second value indicative of the amount of HbA1c,
    the value of the parameter is estimated based on a first value indicative of the amount of HbA1c, and
    the weighted average is determined based on times at which the values indicative of blood glucose concentration are measured relative to a time at which the first value indicative of the amount of HbA1c is measured.

10. The method of claim 1, wherein the value indicative of the amount of HbA1c is measured from a blood sample of the subject including the population of red blood cells, the value indicative of the amount of HbA1c being indicative of an average the amount of HbA1c of the population of red blood cells.

11. The method of claim 1, further comprising determining a subject-specific relationship between values indicative of blood glucose concentration and values indicative of the amount of HbA1c for the subject based on the parameter, wherein the value of the AG is estimated based on the subject-specific relationship.

12. The method of claim 11, wherein the subject-specific relationship is defined by at least one of a value of a glycation rate constant or a value of a reticulocyte HbA1c amount.

13. The method of claim 11, wherein the subject-specific relationship is a linear relationship between the values indicative of AG and the values indicative of the amount of HbA1c.

14. The method of claim 13, wherein the parameter defines a slope of the linear relationship between the values indicative of AG and the values indicative of the amount of HbA1c.

15. The method of claim 1, further comprising determining a diagnostic threshold for the hyperglycemia condition based on the parameter and the estimated value of AG, wherein administering the amount of insulin or insulin analog to the subject to treat the hyperglycemia condition of the subject comprises administering the amount of insulin or insulin analog to the subject to treat the hyperglycemia condition of the subject in response to the value indicative of the amount of HbA1c being above the diagnostic threshold.

16. A method comprising:
    estimating a value of a parameter indicative of an age or lifespan of a population of red blood cells of a subject;
    estimating a value of an amount of HbA1c of the subject based on (i) the value of the parameter and (ii) a value indicative of blood glucose concentration of the subject; and
    administering an amount of insulin or insulin analog to the subject to treat a hyperglycemia condition of the subject, the amount of the insulin or insulin analog being a function of the estimated value of the amount of HbA1c.

17. A method comprising:
    estimating a value of a parameter indicative of an age or lifespan of a population of red blood cells of a subject based on a value indicative of an amount of HbA1c and a value indicative of a blood glucose concentration of the subject; and
    administering an amount of erythropoiesis stimulating agents (ESA) or iron supplementation to the subject to treat anemia of the subject, the amount of the ESA or iron supplementation being a function of the estimated value of the parameter.

* * * * *

UNITED STATES PATENT AND TRADEMARK OFFICE
CERTIFICATE OF CORRECTION

PATENT NO. : 10,955,423 B2
APPLICATION NO. : 16/061951
DATED : March 23, 2021
INVENTOR(S) : Roy Malka, John M. Higgins and David M. Nathan Page 1 of 1

It is certified that error appears in the above-identified patent and that said Letters Patent is hereby corrected as shown below:

In the Claims

In Column 38, Line 21 (approx.), Claim 13, after "between" delete "the"

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*